US011193103B2

(12) United States Patent
Angelini et al.

(10) Patent No.: US 11,193,103 B2
(45) Date of Patent: Dec. 7, 2021

(54) PERFUSION BIOREACTOR AND RELATED METHODS OF USE

(71) Applicant: Regeneron Pharmaceuticals, Inc., Tarrytown, NY (US)

(72) Inventors: Matthew Angelini, Ossining, NY (US); Ashley Witmer, New York, NY (US); Anthony Debiase, Thornwood, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 114 days.

(21) Appl. No.: 16/160,465

(22) Filed: Oct. 15, 2018

(65) Prior Publication Data
US 2019/0153381 A1 May 23, 2019

Related U.S. Application Data

(60) Provisional application No. 62/572,918, filed on Oct. 16, 2017.

(51) Int. Cl.
C12M 1/00 (2006.01)
C12M 1/34 (2006.01)

(52) U.S. Cl.
CPC .......... C12M 41/46 (2013.01); C12M 21/14 (2013.01); C12M 29/04 (2013.01); C12M 29/10 (2013.01); C12M 41/14 (2013.01); C12M 41/26 (2013.01); C12M 41/30 (2013.01); C12M 41/32 (2013.01); C12M 41/38 (2013.01); C12M 43/00 (2013.01)

(58) Field of Classification Search
None
See application file for complete search history.

(56) References Cited

U.S. PATENT DOCUMENTS

| 6,544,424 B1 | 4/2003 | Shevitz |
| 9,109,193 B2 | 8/2015 | Galliher et al. |
| 9,260,695 B2 | 2/2016 | Crowley et al. |
| 9,650,412 B2 * | 5/2017 | Konstantinov .... B01D 15/3814 |
| 9,670,520 B2 | 6/2017 | Zijlstra et al. |
| 10,118,149 B2 | 11/2018 | Reintjens et al. |
| 10,214,718 B2 | 2/2019 | Berteau et al. |
| 2013/0017577 A1 | 1/2013 | Arunakumari et al. |
| 2015/0210971 A1 | 7/2015 | Baskar et al. |
| 2016/0025633 A1 * | 1/2016 | Moretto ..................... G01J 3/44 435/34 |
| 2016/0145563 A1 | 5/2016 | Berteau et al. |
| 2016/0244725 A1 | 8/2016 | Lawrence et al. |
| 2017/0355947 A9 | 12/2017 | Berry et al. |
| 2019/0137338 A1 | 5/2019 | Webster et al. |

FOREIGN PATENT DOCUMENTS

| EP | 2726600 B1 | 2/2017 |
| WO | 2005/084696 A1 | 9/2005 |
| WO | 2005/095578 A1 | 10/2005 |
| WO | 2006/071716 A2 | 7/2006 |
| WO | 2008/006494 A1 | 1/2008 |
| WO | 2010/016943 A2 | 2/2010 |
| WO | 2013/103901 A1 | 7/2013 |
| WO | 2014/059035 A1 | 4/2014 |
| WO | 2015/095809 A1 | 6/2015 |
| WO | 2016/004322 A2 | 1/2016 |
| WO | 2016/196261 A1 | 12/2016 |
| WO | 2016/196315 A2 | 12/2016 |
| WO | 2017/076834 A1 | 5/2017 |
| WO | 2017/132185 A1 | 8/2017 |

OTHER PUBLICATIONS

Ozturk et al. "Real-Time Monitoring and Control of Glucose and Lactate Concentrations in a Mammalian Cell Perfusion Reactor". Biotechnology and Bioengineering. 1997, vol. 53, No. 4, pp. 372-378.*
Inn H. Yuk et al., "Controlling Glycation of Recombinant Antibody in Fed-Batch Cell Culture", Biotechnology and Bioengineering, vol. 108, No. 11, Nov. 2011, pp. 2600-2610 (11 pages).
International Search Report and Written Opinion dated Mar. 21, 2019 in International Application No. PCT/US2018/055891 (19 pages).
Final Office Action dated Nov. 13, 2017 in U.S. Appl. No. 14/127,050 (11 pages).
Karen Bieback et al. (2009) "Human alternatives to fetal bovine serum for the expansion of mesenchymal stromal cells from bone marrow", Stem Cells, vol. 27, No. 9, pp. 2331-2341.
Ana S. Simaria et al. (2014) "Allogeneic cell therapy bioprocess economics and optimization: Single-use cell expansion technologies", Biotechnology and Bioengineering, vol. 111, No. 1, pp. 69-83.
Jong Kwang Hong et al. (2018) "Towards next generation CHO cell line development and engineering by systems approaches", Current Opinion in Chemical Engineering, 22, pp. 1-10.
Ayesha Aijaz et al. (2018) "Biomanufacturing for clinically advanced cell therapies", Nature Biomedical Engineering, vol. 2, No. 6, pp. 362-376.

(Continued)

Primary Examiner — Vera Afremova
(74) Attorney, Agent, or Firm — Bookoff McAndrews, PLLC

(57) ABSTRACT

A method of controlling a bioreactor system includes providing a cell culture in a bioreactor, wherein conditions in the bioreactor enable the cell culture to produce a protein of interest (POI), measuring process parameters (PPs) of the culture within the bioreactor by RAMAN, wherein the process parameters are selected from the group consisting of nutrient concentration, viable cell concentration, and protein attributes, measuring a predetermined weight of the bioreactor with the cell culture, removing cell-free spent media from the cell culture using a first output conduit at a first specified rate, removing cells from the cell culture using a second output conduit at a second specified rate, and introducing one or both of fresh media or nutrients into the cell culture using an input conduit at a third specified rate.

20 Claims, 13 Drawing Sheets

(56) References Cited

OTHER PUBLICATIONS

Mai-Dung Nguyen et al., "Microfluidic Cardiac Circulation Model (μCCM) for Functional Cardiomyocyte Studies", 31st Annual International Conference of the IEEE EMBS, Sep. 2-6, 2009, pp. 1060-1063 (4 pp.).

Michael Pohlscheidt et al., "Optimizing Capacity Utilization by Large Scale 3000 L Perfusion in Seed Train Bioreactors", Biotechnol. Prog., 2013, vol. 29, No. 1, pp. 222-229 (8 pp.).

Yiwen Tao et al., "Development and Implementation of a Perfusion-Based High Cell Density Cell Banking Process", Biotechol. Prog., 2011, vol. 27, No. 3, pp. 824-829 (6pp.).

Xiangming Sun et al., "High-Density Transient Gene Expression in Suspension-Adapted 293 EBNA1 Cells", Biotechnology and Bioengineering, vol. 99, No. 1, Jan. 1, 2008, pp. 108-116 (9 pp.).

Ishai Padawer et al., "Case Study: An Accelerated 8-Day Monoclonal Antibody Production Process Based on High Seeding Densities", Biotechnol Prog., 2013, vol. 29, No. 3, pp. 829-832 (4 pp.).

Christian Kaisermayer et al., "Highly efficient inoculum propagation in perfusion culture using WAVE Bioreactor™ systems", Kaisermayer and Yang BMC Proceedings 2013, 7(Suppl 6):P7, <http://www.biomedcentral.com/1753-6561/7/S6/P7>, From 23rd European Society for Animal Cell Technology (ESACT) Meeting: Better Cells for Better Health Lille, France. Jun. 23-26, 2013, 3 pp.

Konstantin Konstantinov et al. "The 'Push-to-Low' Approach for Optimization of High-Density Perfusion Cultures of Animal Cells", Adv Biochem Engin/Biotechnol (2006) vol. 101, pp. 75-98, Jul. 5, 2006.

Jessica Whelan et al., "In Situ Raman Spectroscopy for Simultaneous Monitoring of Multiple Process Parameters in Mammalian Cell Culture Bioreactors", American Institute of Chemical Engineers, Biotechnol. Prog., 2012, vol. 28, No. 5. pp. 1355-1362.

Jean-Marc Bielser et al., "Perfusion mammalian cell culture for recombinant protein manufacturing—A critical review", Biotechnology Advances, Issue 36, 2018, pp. 1328-1340.

A. DeBiase et al., "Monitoring bioreactor cell culture data in real time—aka—Now that's using your noodle: a RAMAN Story", OSIsoft Users Conference 2017, Mar. 2017, 18 pages.

Aspen Alert e-mail, "The Biotechnology Community, Connected. Every Day." Issue No. 2557, Nov. 17, 2017, 18 pages.

Daniel J. Karst et al., "Characterization and comparison of ATF and TFF in stirred bioreactors for continuous mammalian cell culture processes", Biochemical Engineering Journal, Issue 110, 2016, pp. 17-26.

International Conference on Harmonisation of Technical Requirements for Registration of Pharmaceuticals for Human Use, ICH Harmonised Tripartite Guideline, Pharmaceutical Development Q8(R2), Current Step 4 version dated Aug. 2009, 28 pages.

Beum Jun Kim et al., "Batch, Fed-Batch, and Microcarrier Cultures With CHO Cell Lines in a Pressure-Cycle Driven Miniaturized Bioreactor", Biotechnology and Bioengineering, vol. 109, No. 1, Jan. 2012, pp. 137-145 (9 pages).

Takeshi Omasa et al., "Cell Engineering and Cultivation of Chinese Hamster Ovary (CHO) Cells", Current Pharmaceutical Biotechnology, 2010, vol. 11, No. 3, pp. 233-240 (9 pages).

* cited by examiner

PERFUSION BIOREACTOR AND RELATED METHODS OF USE

CROSS-REFERENCE TO RELATED APPLICATION(S)

This patent application claims the benefit under 35 U.S.C. § 119 to U.S. Provisional Patent Application No. 62/572,918, filed on Oct. 16, 2017, the entirety of which is incorporated herein by reference.

TECHNICAL FIELD

This disclosure is directed to a perfusion bioreactor and related methods of use.

BACKGROUND

Bioreactors can be used to maintain a cell culture for the purpose of manufacturing biological products such as proteins. In a fed-batch bioreactor, one or more nutrients are fed to the bioreactor during cultivation, and the biological products remain in the bioreactor until the end of the batch. Perfusion bioreactors address some of the performance challenges related to fed-batch reactors, and started gaining popularity in the late 1990s. However, state-of-the-art perfusion bioreactors suffer from a limited number of available control strategies, data gaps, and high expense.

For example, control solutions for perfusion reactors attempt to calibrate the volumetric flow of the input and output feed pumps, while addressing pump drift and process variability. However, failed production runs may result in the overfilling or emptying of the bioreactor, due to inherent differences (e.g., manufacturing variances) between any two given pumps and inability to achieve tight control. Existing control solutions also lack the ability to measure other parameters, such as, e.g., ammonia, glucose, and protein quality attributes. Embodiments of the present disclosure address one or more of the limitations and drawbacks of existing perfusion bioreactors.

SUMMARY OF THE DISCLOSURE

Embodiments of the present disclosure relate to, among other things, a method of controlling a bioreactor and a bioreactor system useful for controlling the cell culture process for protein production. Each of the embodiments disclosed herein may include one or more of the features described in connection with any of the other embodiments.

The disclosure is related to a method of controlling a bioreactor system, comprising providing a cell culture in a bioreactor; measuring one or more process parameters of the cell culture within the bioreactor by a RAMAN probe; removing cell-free spent media from the cell culture using a first output conduit at a first specified rate; removing cells from the cell culture using a second output conduit at a second specified rate; introducing one or both of fresh media or nutrients into the cell culture using an input conduit at a third specified rate; and changing one or more of the first specified rate, the second specified rate, or the third specified rate based on the RAMAN probe measurements.

One embodiment of the disclosure is directed to a method of controlling a bioreactor system which comprises providing a cell culture in the bioreactor, wherein conditions in a bioreactor enable the cell culture to produce a protein of interest (POI), measuring process parameters (PPs) of the culture within the bioreactor by RAMAN, wherein the process parameters are selected from the group consisting of nutrient concentration, viable cell concentration, and protein attributes, measuring a weight of the bioreactor with cell culture contents, removing cell-free spent media from the cell culture using a first output conduit at a first specified rate, removing cells from the cell culture using a second output conduit at a second specified rate, introducing one or both of fresh media and nutrients into the cell culture using an input conduit at a third specified rate, and wherein the input and output conduits are adjusted based on the RAMAN probe measurements and weight measurement of the bioreactor to maintain (i) one or more of the process parameters within predetermined ranges, (ii) the weight of the bioreactor with the cell culture within predetermined ranges, and (iii) the third specified rate of the input conduit and the first and second specified rates of each of the output conduits within their respective predetermined ranges.

In some embodiments, measuring the one or more process parameters of the culture within the bioreactor by RAMAN occurs at regular intervals, e.g. least once per hour. In other embodiments, the method is configured to maintain the cell culture at an average viable cell concentration of at least about 30 million cells per mL for at least about 30 days at steady state. In one embodiment, the bioreactor has a volume of at least 2 L, at least 3 L, at least 10 L, at least 35 L, or at least 50 L, or more, and the method is configured to maintain the weight of the bioreactor with the cell culture within 0.1 percent of an initial weight of the bioreactor with the cell culture. For example, the bioreactor has a volume of at least about 10 L, and the method is configured to maintain the weight of the bioreactor and cell culture within a weight range determined based on the initial weight of the bioreactor and the cell culture contents, e.g. about within a 20±2 g range. In some embodiments, the bioreactor is controlled when a process parameter deviates from a set point value within a respective desired range, one or more of removing cell-free media, removing cells, and introducing one or both of fresh media and nutrients, and then the bioreactor is adjusted to reduce the deviation. At least two bioreactor volumes of spent media is removed through the first output conduit per day. Up to three bioreactor volumes of spent media is removed through the first output conduit per day. The process parameters includes temperature of the cell culture and pH of the cell culture, and the temperature is maintained from about 30 to 40 degrees C., from about 32 to about 38 degrees C., or from about 34 to about 38 degrees C., and the pH is maintained from about 6.50 to about 7.50, from about 6.60 to about 7.40, from about 6.70 to about 7.40, from about 6.80 to about 7.30 from about 6.90 to about 7.20, from about 7.00 to about 7.10, at about 6.50, at about 6.55, at about 6.60, at about 6.65, at about 6.70, at about 6.75, at about 6.80, at about 6.85, at about 6.90, at about 6.95, at about 7.00, at about 7.05, at about 7.10, at about 7.15, at about 7.20, at about 7.25, at about 7.30, at about 7.35, at about 7.40, at about 7.45, or at about 7.50. The process parameters include cell specific productivity, and the method is configured to maintain cells within the cell culture at a cell specific productivity of at least about 15-60 pg/cell/day, about 15-25 pg/cell/day, at least about 17-23 pg/cell/day, or at least about 19-21 pg/cell/day for at least 25-37 days. The process parameters include glucose concentration, and the method is configured to maintain a glucose concentration from about 5 mM to about 85 mM, or from about 0.5 g/L to about 15.5 g/L, from about 1 g/L to about 15.5 g/L, from about 0.5 g/L to about 8 g/L, from about 2 g/L to about 6 g/L, or from about 3 g/L to about 5 g/L. The process parameters include lactate concentration, and the method is configured to maintain a lactate concentration less than about 60 mM, or less than about 6 g/L, less than about 5 g/L, less than about 4 g/L, less than about 3 g/L, less than about 2 g/L, or less than about 1 g/L. The process parameters include ammonia concentration, and the method is configured to maintain an ammonia concentration less than about 15 mM, less than about 12 mM, less than about 10 mM, less than about 9 mM, less than about 8 mM, less than about 7 mM, less than about 6 mM. Each of removing cell-free spent media, removing cells, and introducing one or both of fresh media and nutrients, is controlled by a respective pump. The bioreactor includes a filter configured to retain cells and allow fluid to pass through.

In another embodiment, the disclosure is directed to method of controlling a bioreactor system, comprising providing a cell culture in a bioreactor; measuring one or more process parameters (PPs) of the cell culture within the bioreactor by a RAMAN probe; and adjusting one or more inputs or outputs of the bioreactor based on measurements from the RAMAN probe.

The method according to the disclosure is illustrated as comprising the following steps: providing a cell culture in the bioreactor (302), wherein conditions in the bioreactor enable the cell culture to produce a protein of interest (POI), measuring process parameters of the culture within the bioreactor by RAMAN (304), wherein the process parameters are selected from at least the group consisting of nutrient concentration, viable cell concentration, and protein attributes, measuring a predetermined weight of the bioreactor with the cell culture (306), removing cell-free spent media from the cell culture using a first output conduit at a first specified rate (308), removing cells from the cell culture using a second output conduit at a second specified rate (310), introducing one or both of fresh media and nutrients into the cell culture using an input conduit at a third specified rate, and wherein input and output conduits are adjusted based on the RAMAN probe measurements and weight measurement of the bioreactor to maintain (i) one or more of the process parameters within predetermined ranges, (ii) the weight of the bioreactor with the cell culture within predetermined ranges, and (iii) the third specified rate of the input conduit and the first and second specified rates of each of the output conduits within their respective predetermined ranges (312).

In yet another aspect, the disclosure is directed to a bioreactor culture system, comprising a tank having an input conduit and at least one output conduit; at least one pump; a filter coupled to the tank; a RAMAN probe coupled to the tank; and a controller coupled to the at least one pump and the RAMAN probe, the controller being configured to control the at least one pump based on an input from the RAMAN probe.

The at least one output conduit includes a first output conduit for connection to a second pump configured to control removal of fluid from the tank, and a second output conduit for connection to a third pump configured to control removal of cells from the tank. The filter is configured to retain cells in the tank and to allow fluid to pass through the filter. The RAMAN probe is disposed within the tank. The controller is coupled to first pump, the second pump, and the third pump. The bioreactor includes a scale configured to measure a weight of the tank with a cell culture within the tank; wherein the controller is configured to receive weight data from the scale. The controller is configured to compare the weight of the tank with a set point for the weight, and based on the comparison, adjust one or more of an output of the first pump, the second pump, and the third pump. The controller is configured to receive spectral data from the RAMAN probe; determine, based on the received spectral data, a parameter of the cell culture; compare the determined parameter to a set point of the parameter; and based on the comparison, adjust one or more of an output of the first pump, the second pump, or the third pump. Adjusting the output of one or more of the first pump, the second pump, and the third pump, reduces a deviation between the determined parameter and the set point of the parameter, or a deviation between the received weight and the set point of the weight. The method is configured to maintain the cell culture at an average viable cell concentration of at least 30 million cells per mL for 30 days at steady state. The tank has a volume of at least 10 L, and the method is configured to maintain the weight of the tank with the cell culture within a 20 g range. The tank has a volume of at least 10 L, and the method is configured to maintain the weight of the bioreactor with the cell culture within 0.1 percent of an initial weight of the tank with the cell culture. The controller is configured to determine, based on the received spectral data, a plurality of parameters of the bioreactor culture; compare each of the plurality of parameters to a respective set point for each of the plurality of parameters; and based on the comparison, adjust the output of one or more of the first pump, the second pump, and the third pump, to reduce a deviation between the determined parameters and the respective set points. The plurality of parameters includes temperature, pH, nutrient concentration, lactate concentration, ammonia concentration, and cell specific productivity. The filter is configured to retain cells and allow fluid to pass through. The bioreactor includes a scale, wherein the tank and the filter rest on the scale. The bioreactor includes a scale, wherein the tank rests on the scale. The bioreactor includes a scale, wherein the tank is in physical contact with the scale.

A bioreactor culture system, comprising: a tank having an input conduit and at least one output conduit; at least one pump; a filter in contact with the tank; a RAMAN probe coupled to the tank; a scale in contact with the tank; and a controller coupled to the at least one pump, the scale, and the RAMAN probe. In some embodiments, the filter and the tank are in contact with the scale. In another embodiment, the filter comprises mesh material. In some embodiments, the filter comprises mesh having pore sizes ranging from 0.2 µM to 30 µM.

In yet another embodiment, the disclosure is directed to a bioreactor culture system, comprising a tank having an input conduit and at least one output conduit; at least one pump; a filter coupled to the tank; a scale in contact with the tank; a RAMAN probe coupled to the tank; and a controller coupled to the at least one pump, the scale, and the RAMAN probe, the controller being configured to control the at least one pump based on an input from the RAMAN probe and an input from the scale.

In another embodiment, a bioreactor culture system is disclosed. The bioreactor culture system includes a tank having an input conduit for connection to a first pump configured to control fluid delivery to the tank, a first output conduit for connection to a second pump configured to control removal of fluid from the tank, and a third output conduit for connection to a third pump configured to control removal of cells from the tank, a filter coupled to the tank, wherein the filter is configured to retain cells in the tank and to allow fluid to pass through the filter, a scale configured to measure a weight of the tank with a cell culture within the tank, a RAMAN probe disposed within the tank. The embodiment includes a controller coupled to the first pump, the second pump, the third pump, the scale, and the RAMAN probe, wherein the controller is configured to receive weight data from the scale, compare the weight of the tank with a set point for the weight, receive spectral data from the RAMAN probe, determine, based on the received spectral data, a parameter of the cell culture, compare the determined parameter to a set point of the parameter, and based on the comparisons, adjust one or more of a throughput of the first pump, the second pump, and the third pump.

Adjusting the throughput of one or more of the first pump, the second pump, and the third pump, reduces a deviation between the determined parameter and the set point of the parameter, or a deviation between the received weight and the set point of the weight. The controller is configured to maintain the cell culture at an average viable cell concentration of at least 30 million cells per mL for 30 days at steady state. The tank has a volume of at least 3 L, and the controller is configured to maintain the weight of the tank with the cell culture within a 20 g range. The tank has a volume of at least 3 L, and the controller is configured to maintain the weight of the bioreactor with the cell culture within 0.1 percent of an initial weight of the tank with the cell culture. The controller isconfigured to determine, based on the received spectral data, a plurality of parameters of the bioreactor culture, compare each of the plurality of parameters to a respective set point for each of the plurality of parameters, and based on the comparison, adjust the throughput of one or more of the first pump, the second pump, and the third pump, to reduce a deviation between the determined parameters and the respective set points. The plurality of parameters include temperature, pH, nutrient concentration, lactate concentration, ammonia concentration, and cell specific productivity. The bioreactor culture system include a filter configured to retain cells and allow fluid to pass through. The tank and the filter rest on the scale. The tank rests on the scale.

In certain embodiments, the bioreactor culture system according to the disclosure is illustrated as comprising the following elements: a tank (10) having an input conduit for connection to a first pump (30) configured to control fluid delivery to the tank, a first output conduit for connection to a second pump (40) configured to control removal of fluid from the tank, and a third output conduit for connection to a third pump (50) configured to control removal of cells from the tank; filter (100) coupled to, connected to, or otherwise in fluid communication with the tank, wherein the filter is configured to retain cells in the tank and to allow fluid to pass through the filter; a scale (110) configured to measure a weight of the tank with a cell culture within the tank; a RAMAN probe (18) disposed within the tank; and a controller (200) coupled to the first pump (30), the second pump (40), the third pump (50), the scale (110), and the RAMAN probe (18).

In the bioreactor culture system the controller (200) is configured to: receive weight data from the scale (110); compare the weight of the tank (10) with a set point for the weight; receive spectral data from the RAMAN probe (18); determine, based on the received spectral data, a parameter of the cell culture; compare the determined parameter to a set point of the parameter; and based on the comparisons, adjust one or more of a throughput of the first pump, the second pump, and the third pump.

BRIEF DESCRIPTION OF THE FIGURES

The accompanying drawings, which are incorporated in and constitute a part of this specification, illustrate various examples and together with the description, serve to explain the principles of the disclosed examples and embodiments.

Aspects of the disclosure may be implemented in connection with embodiments illustrated in the attached drawings. These drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

Moreover, there are many embodiments described and illustrated herein. The present disclosure is neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended to reflect or indicate the embodiment(s) is/are "example" embodiment(s).

Figure 1:
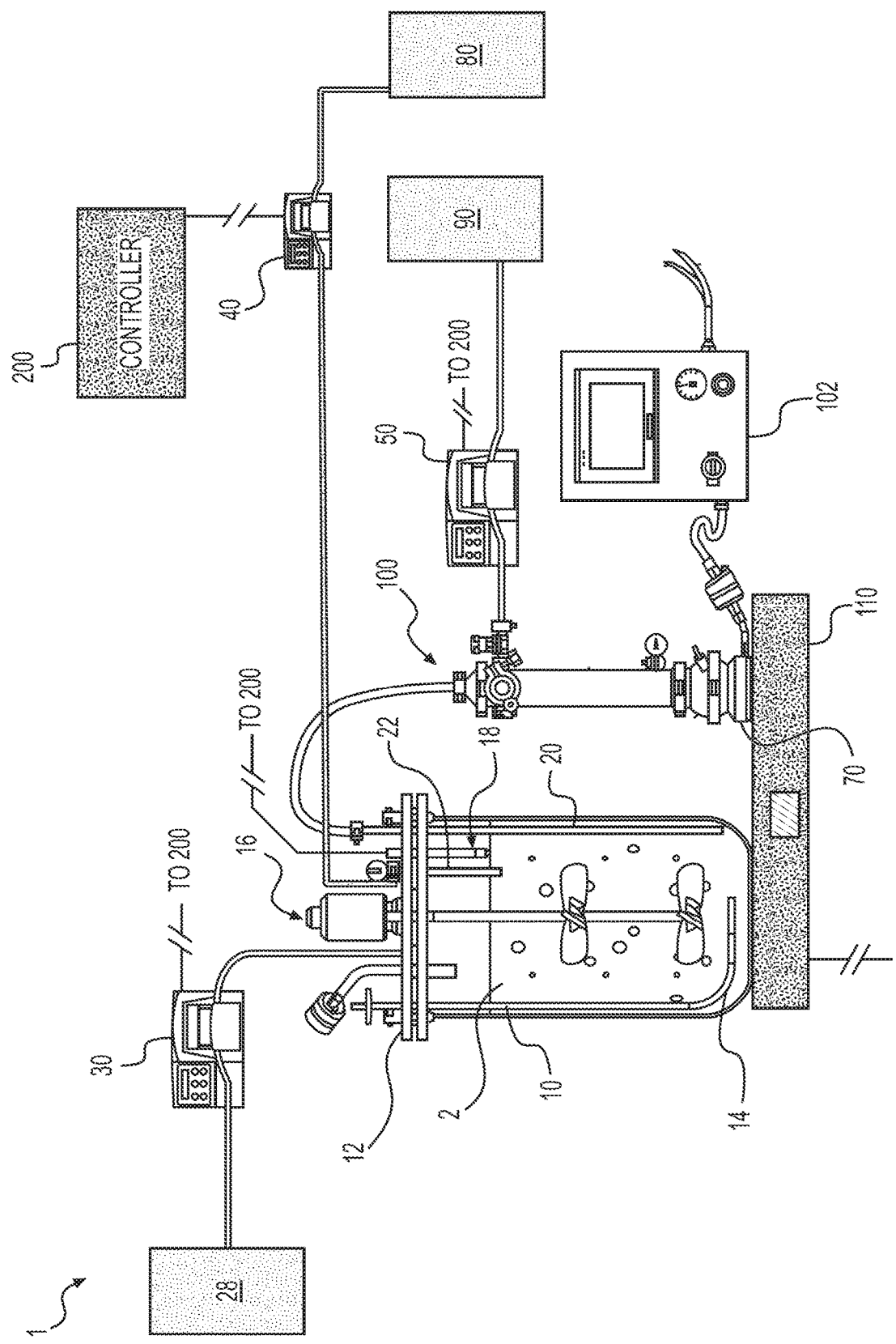

FIG. 1 is a schematic view of a bioreactor system, according to an example of the disclosure.

Figure 2:
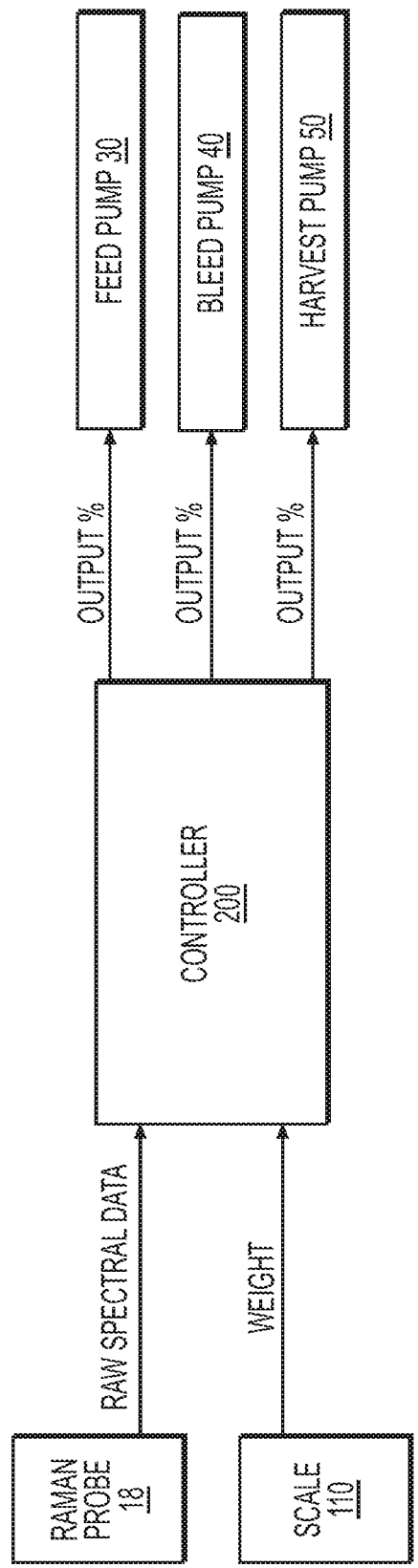

FIG. 2 is schematic view of an exemplary controller of the bioreactor system of FIG. 1, and its respective inputs and outputs.

Figure 3:
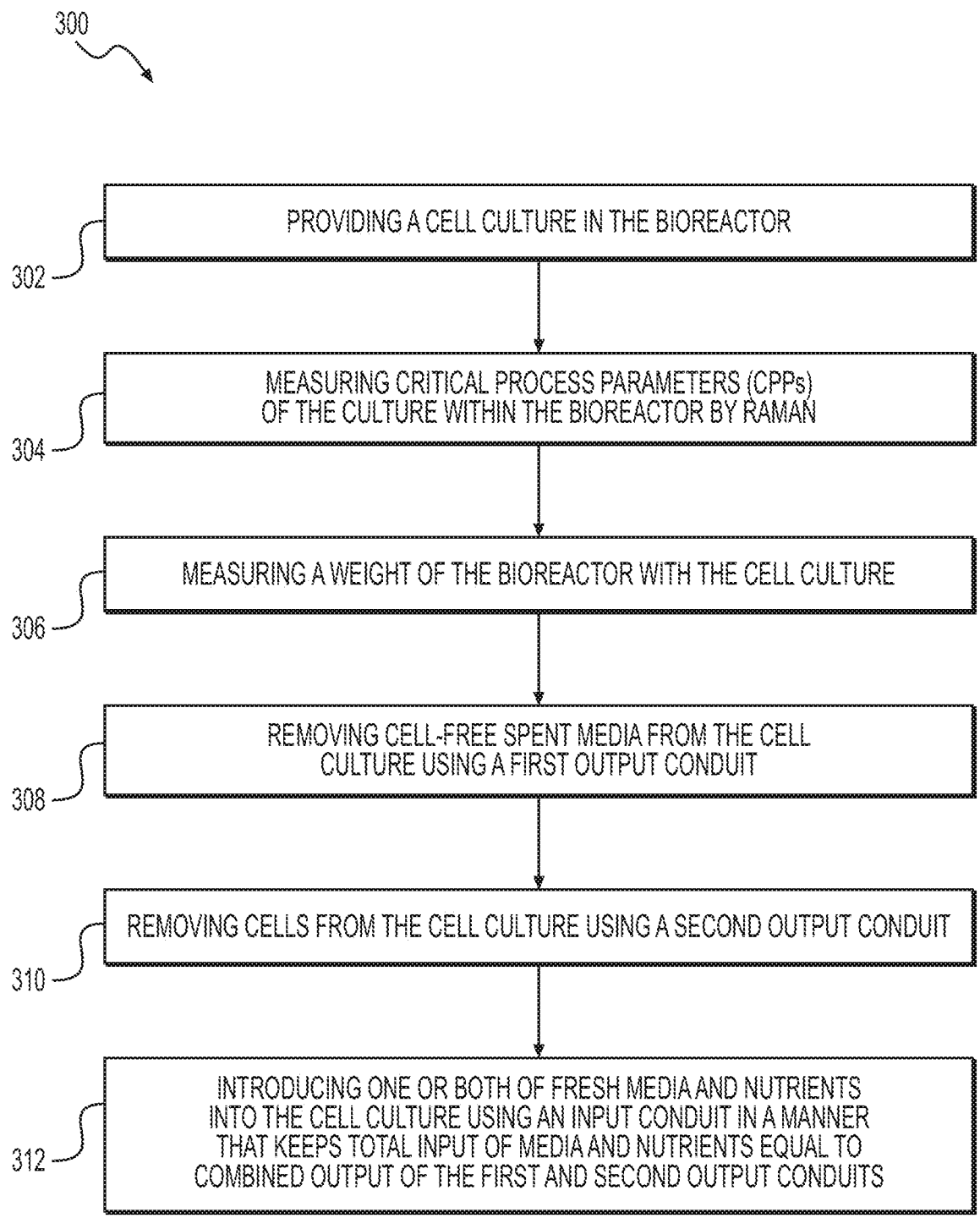

FIG. 3 is a flowchart of an exemplary method according to the disclosure.

Figure 4:
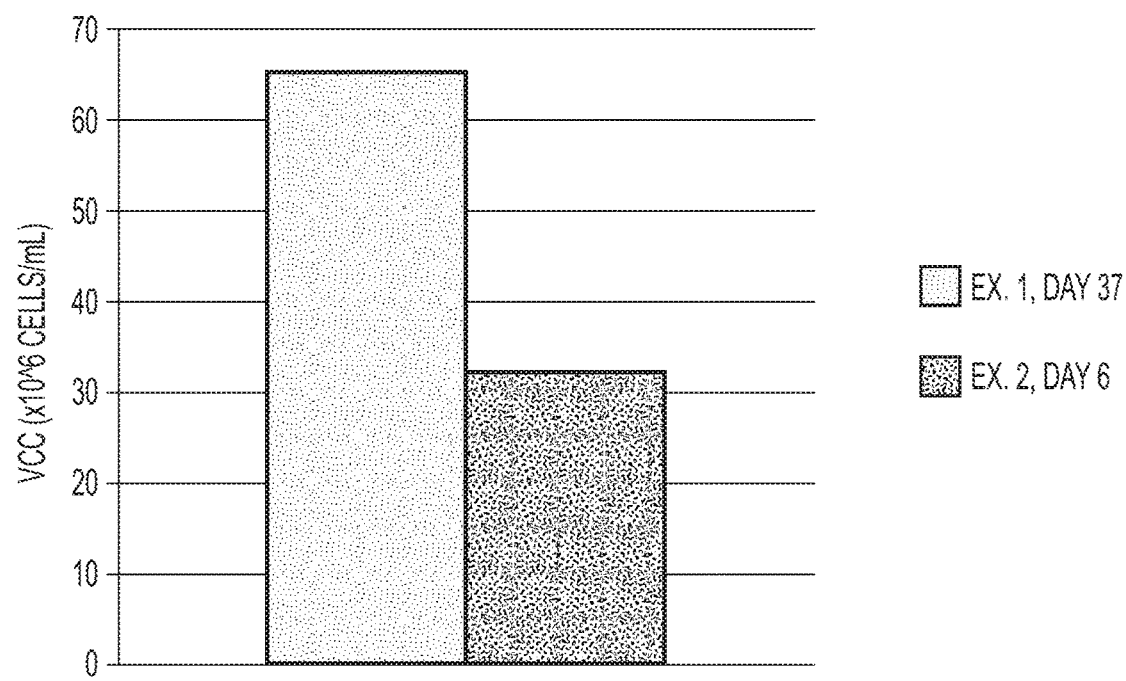

FIG. 4 is a graph comparing measured viable cell concentration in a perfusion bioreactor at day 37 of a batch with measured viable cell concentration in a fed-batch bioreactor at day 6 of a batch.

Figure 5:
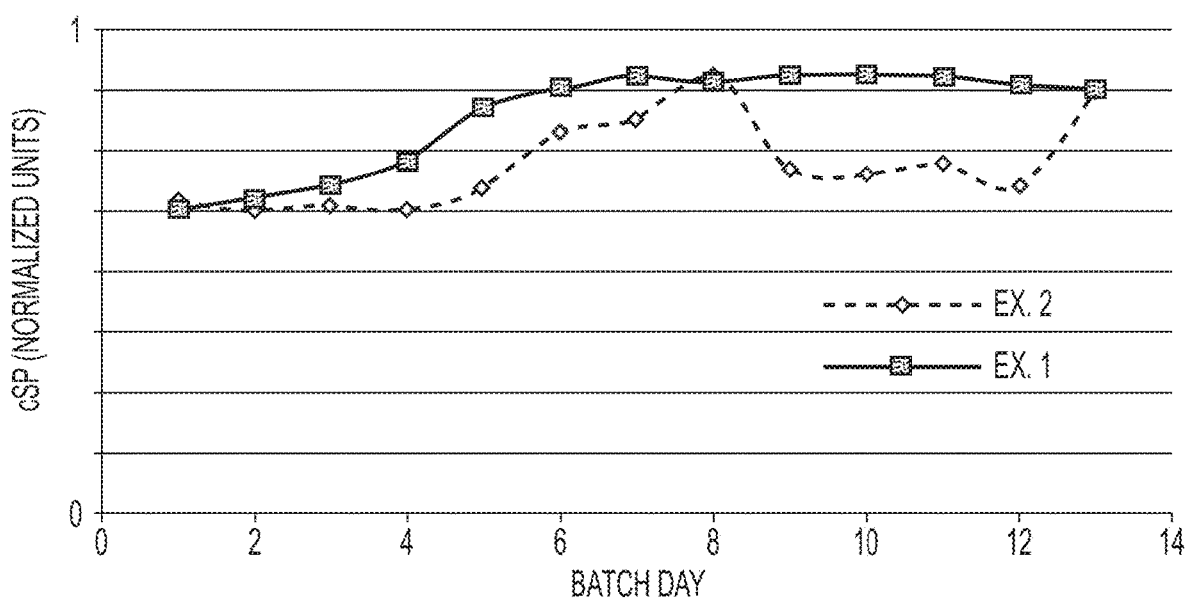

FIG. 5 is a graph showing normalized cell specific productivity over time between the perfusion bioreactor and fed-batch bioreactor described with reference to FIG. 4.

Figure 6:
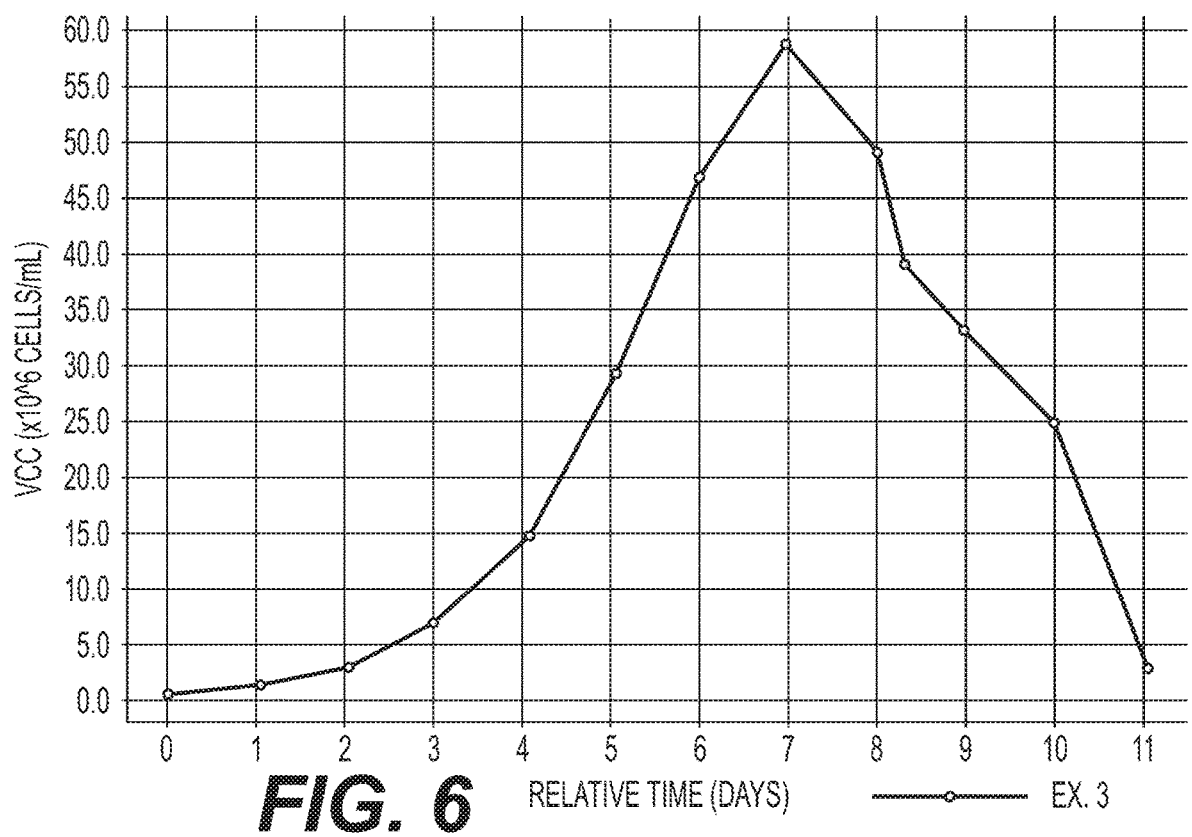

FIG. 6 is a graph showing viable cell concentration over time for a perfusion bioreactor that did not control for viable cell concentration or glucose.

Figure 7:
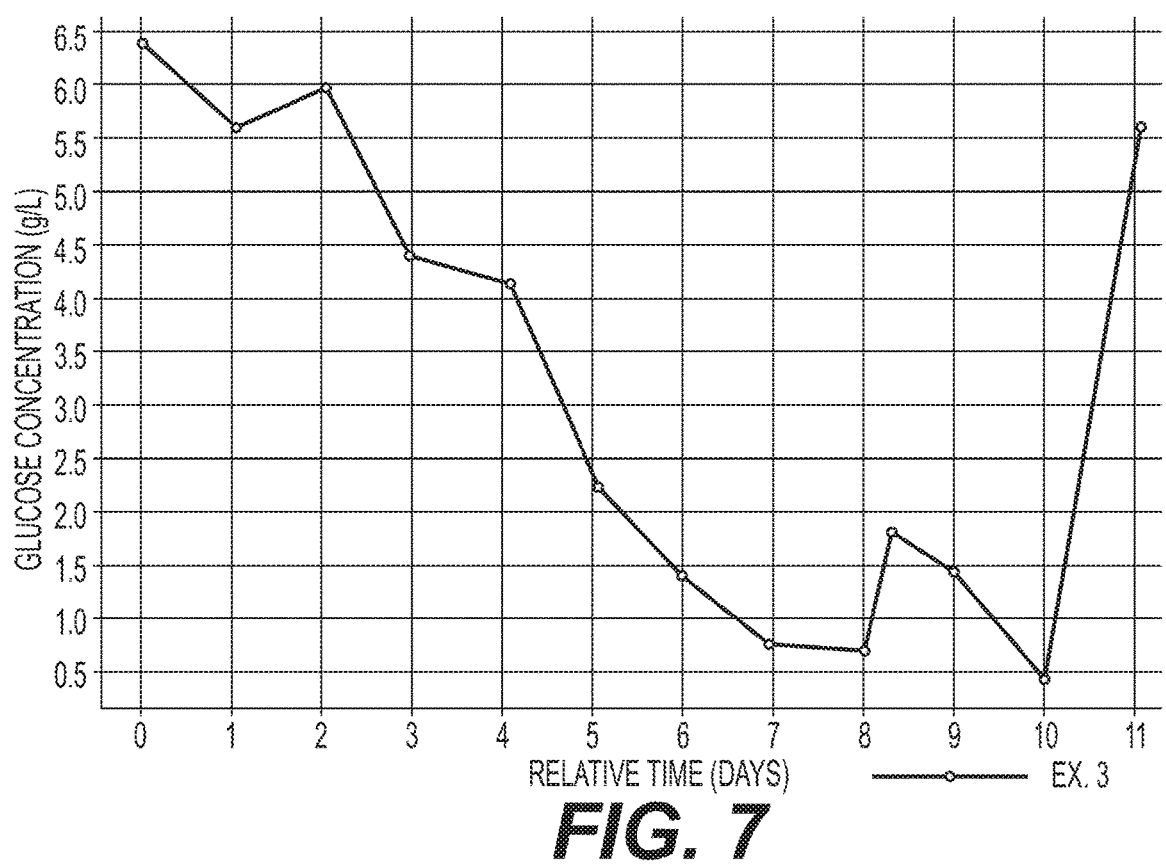

FIG. 7 is a graph showing glucose concentration over time in the perfusion bioreactor described in FIG. 6.

Figure 8:
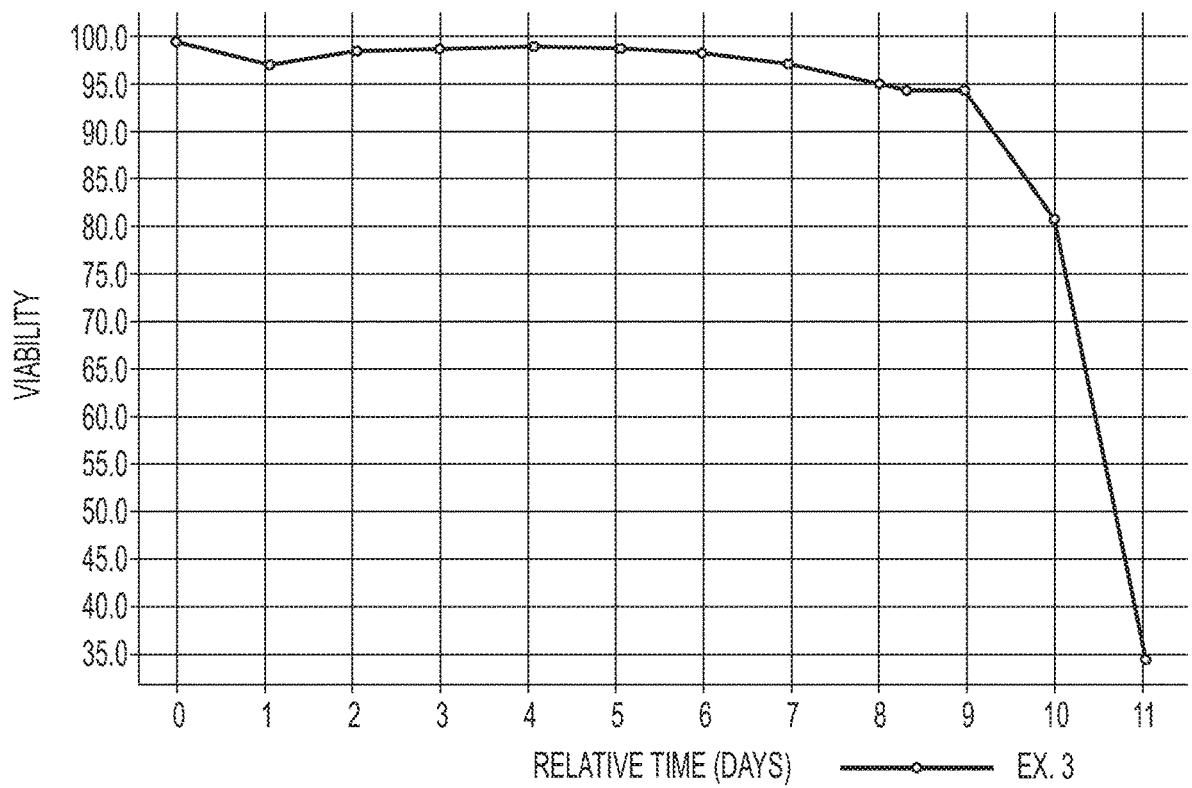

FIG. 8 is a graph showing cell viability over time in the perfusion bioreactor described in FIG. 6.

Figure 9:
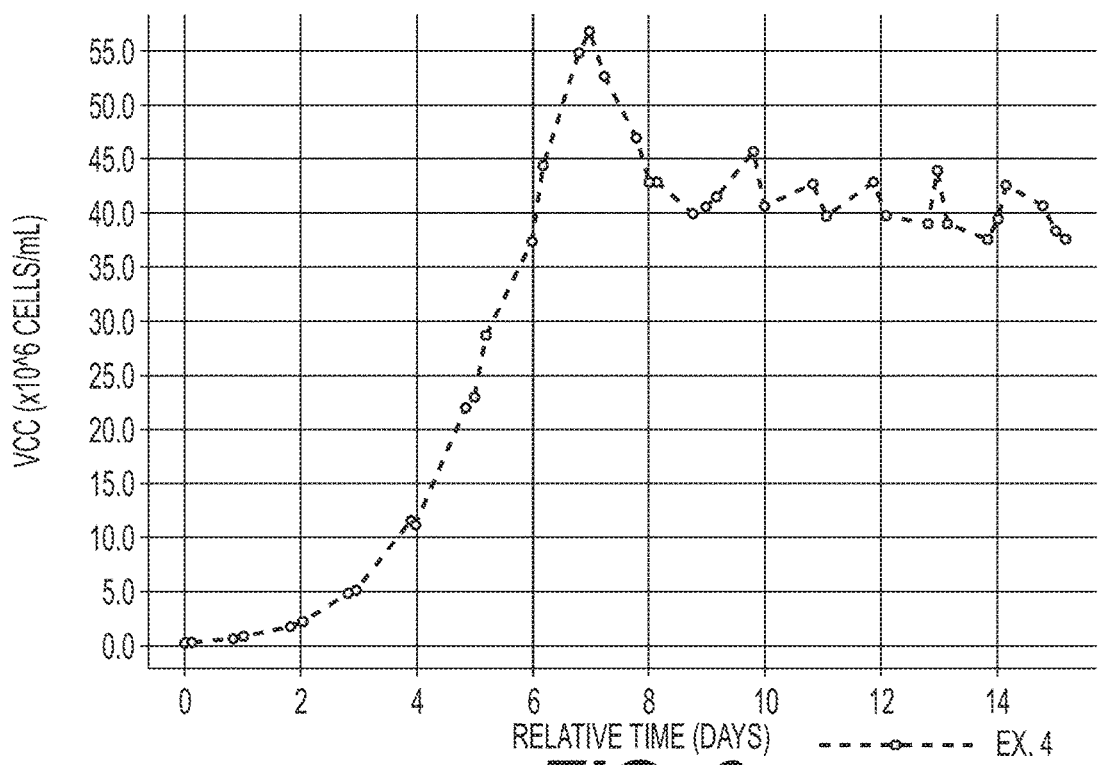

FIG. 9 is a graph showing viable cell concentration over time for a perfusion bioreactor that controlled for viable cell concentration.

Figure 10:
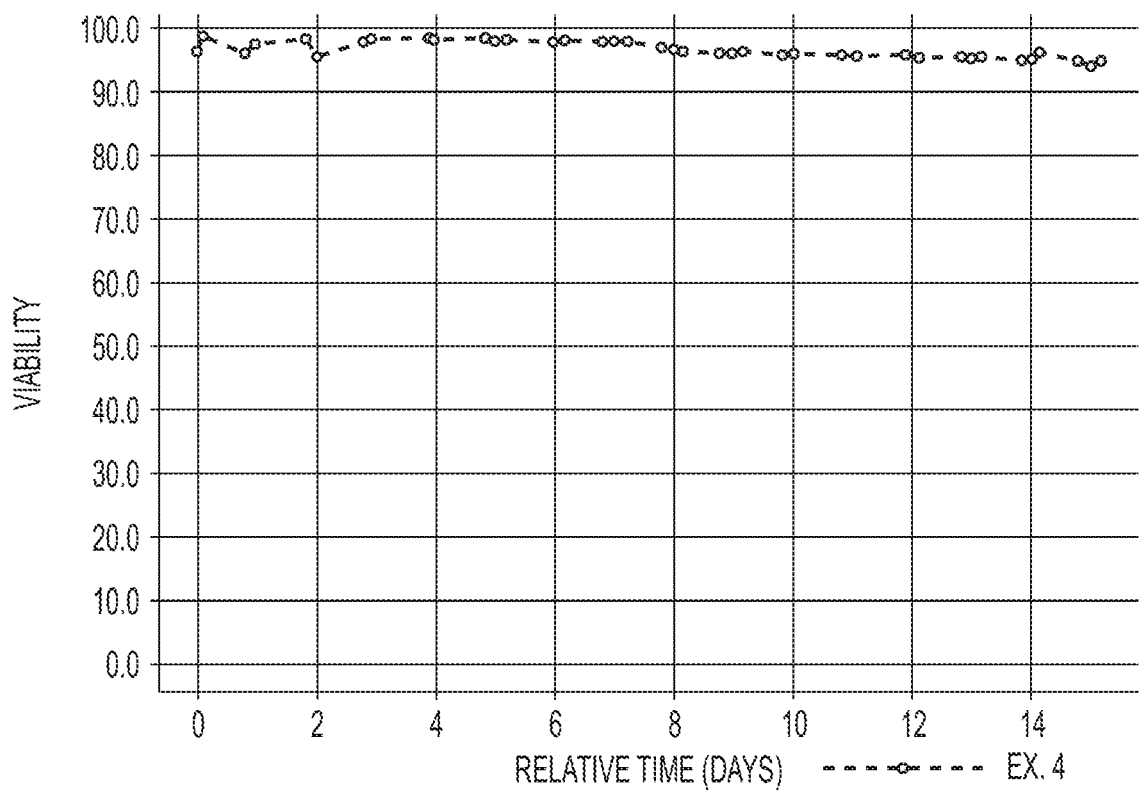

FIG. 10 is a graph showing steady state cell viability in the perfusion bioreactor described in FIG. 9.

Figure 11:
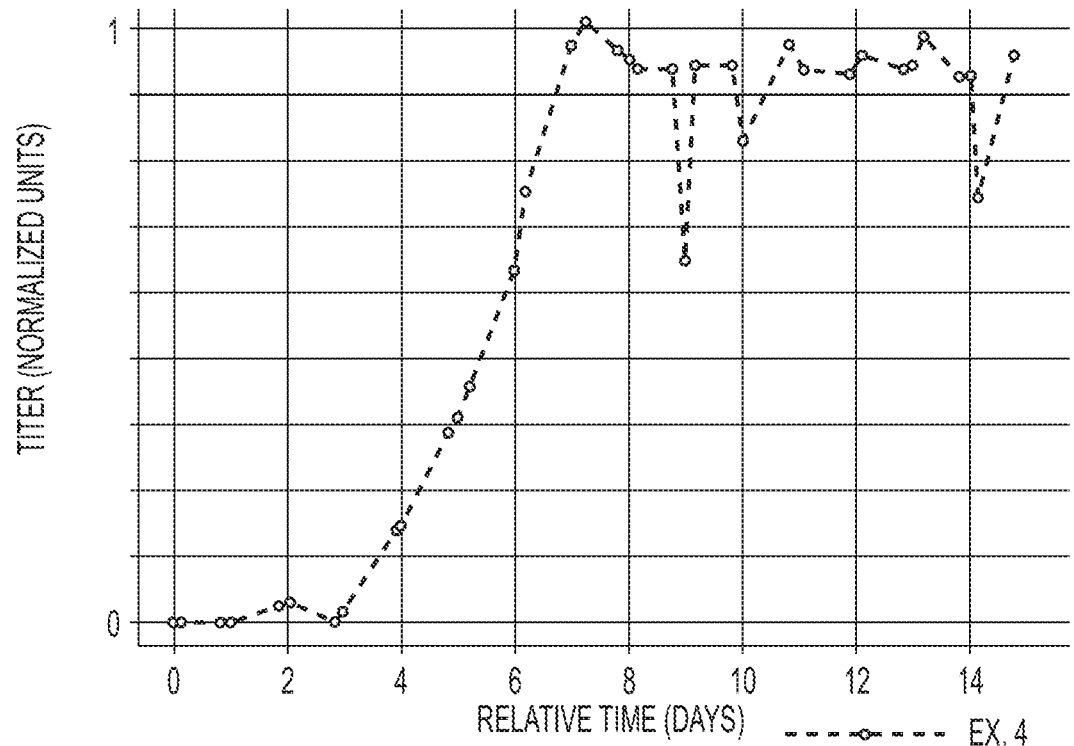

FIG. 11 is a graph showing normalized protein production (titer) over time in the perfusion bioreactor described in FIG. 9.

Figure 12:
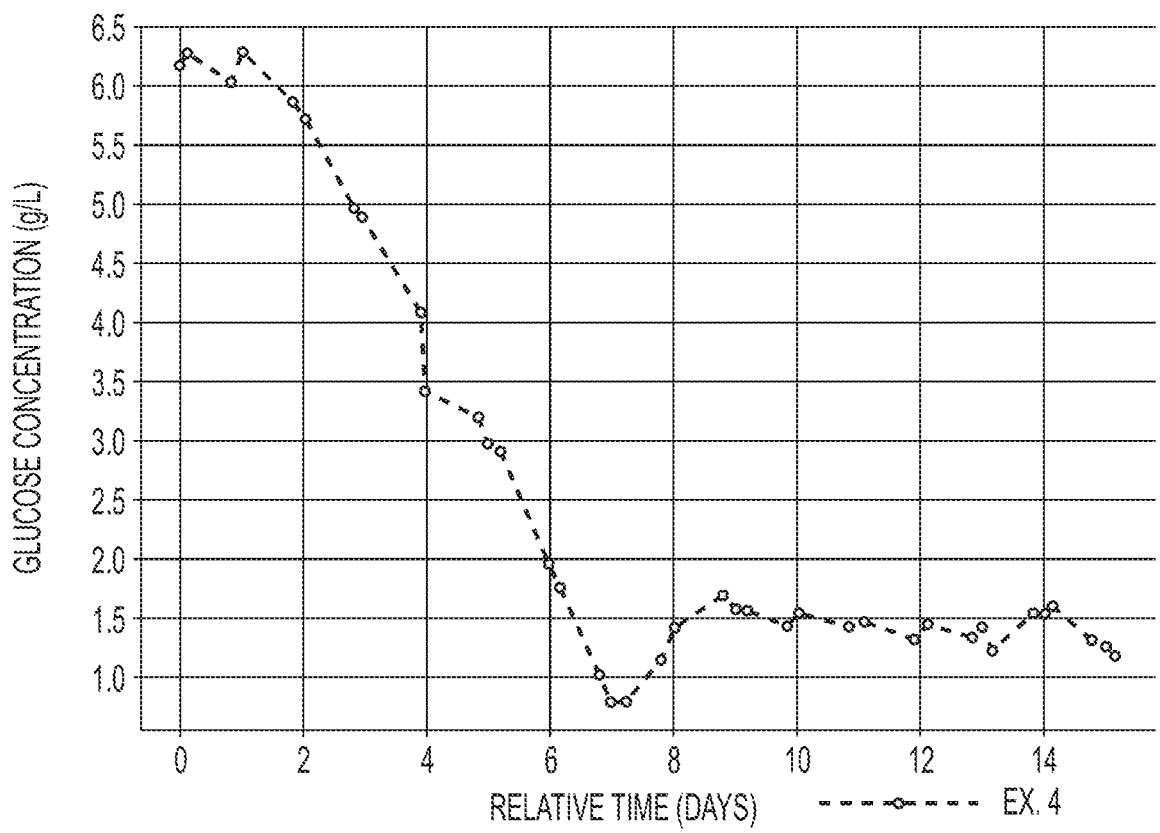

FIG. 12 is a graph showing glucose concentration over time in the perfusion bioreactor described in FIG. 9.

Figure 13:
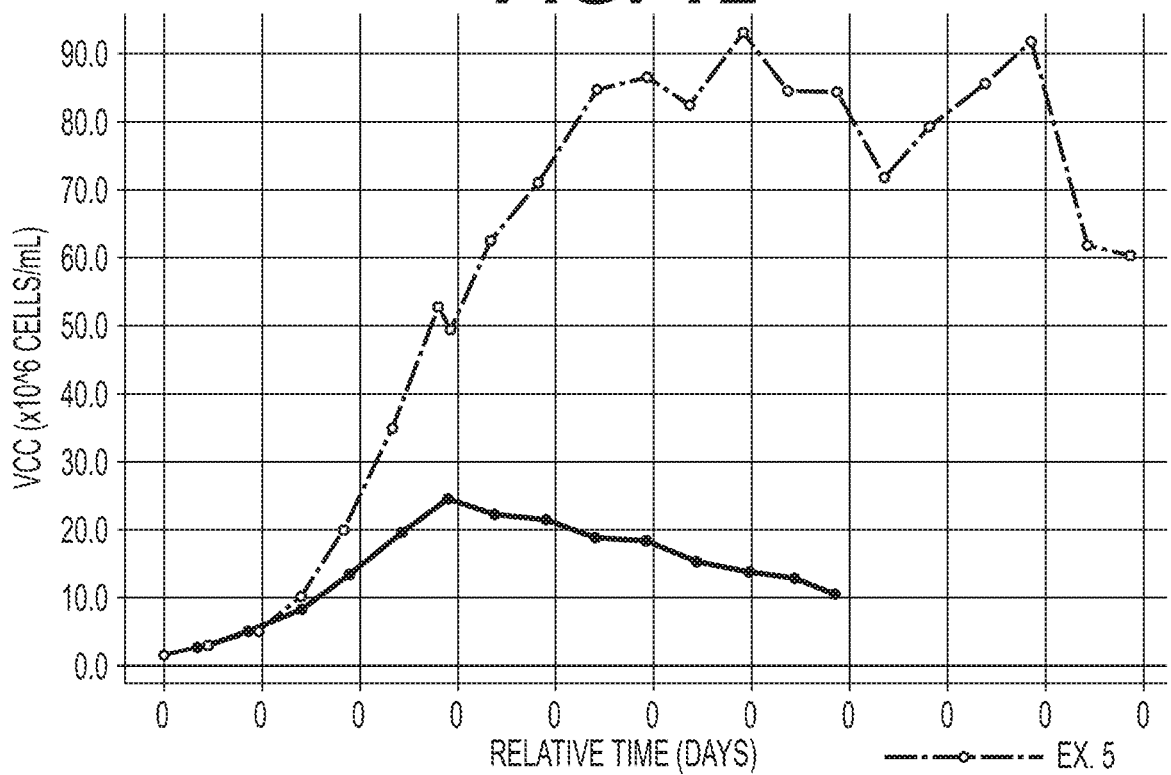

FIG. 13 is a graph comparing viable cell concentrations from a perfusion bioreactor and a fed-batch bioreactor.

Figure 14:
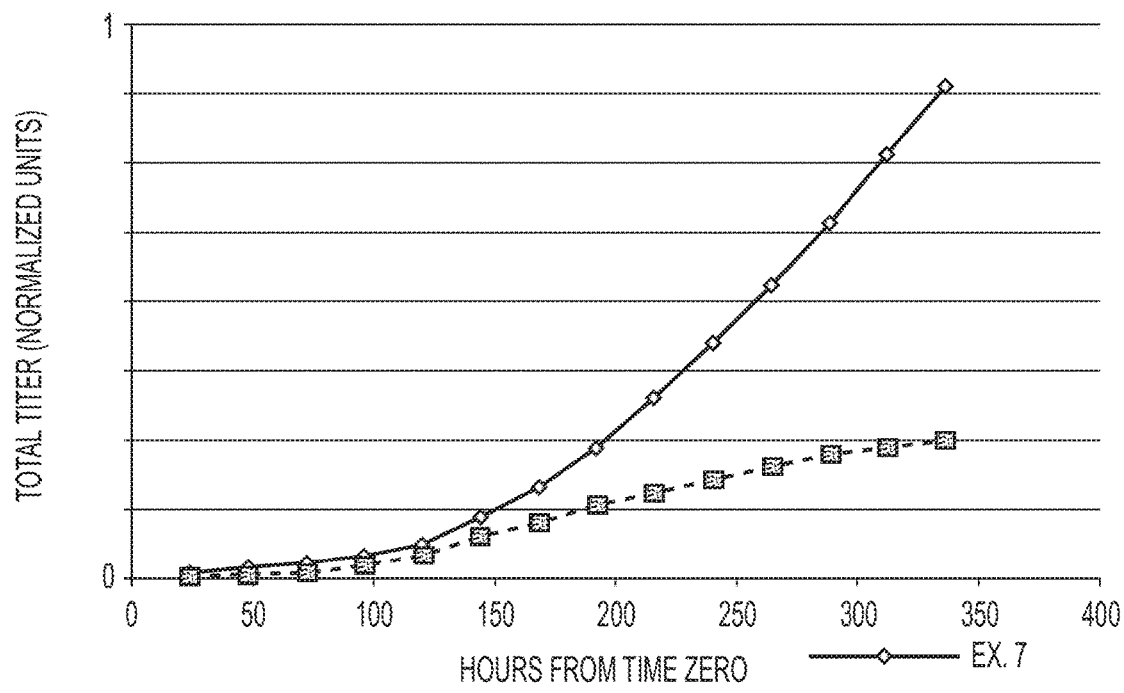

FIG. 14 is a graph comparing normalized protein production (titer) achieved in the bioreactors described in FIG. 13.

Figure 15:
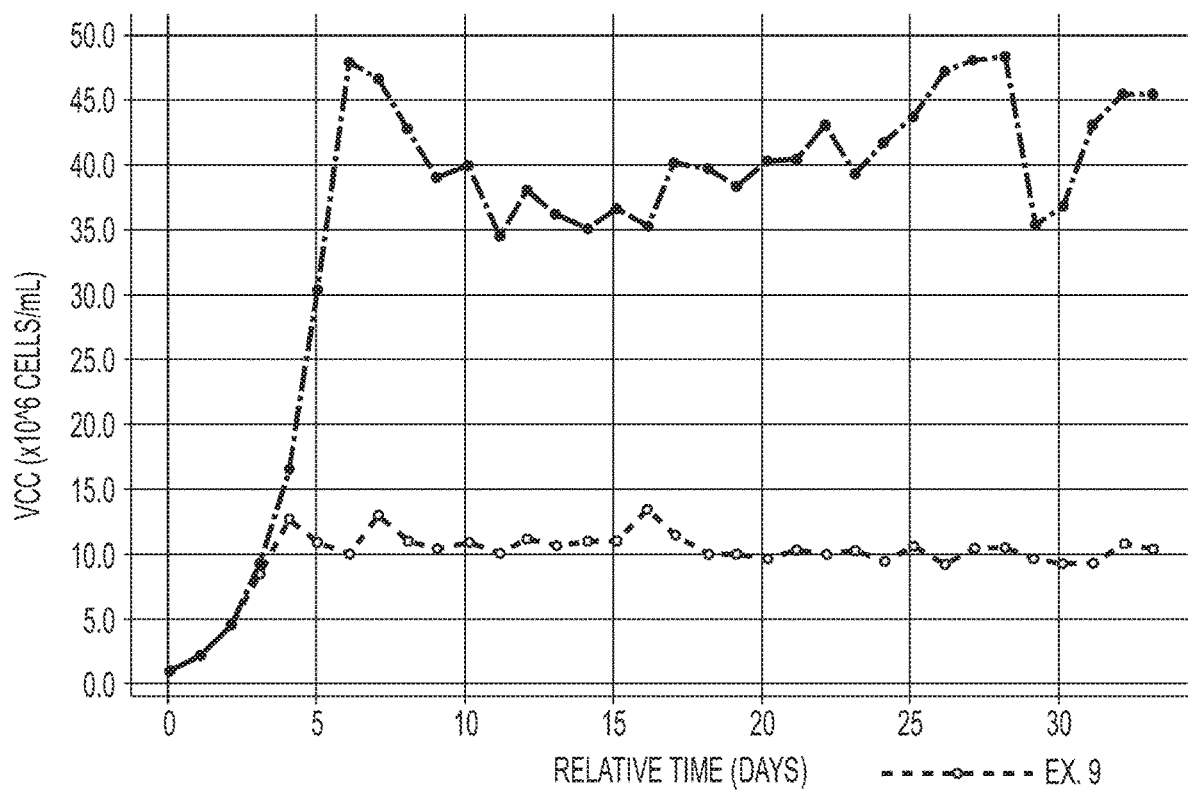

FIG. 15 is a graph showing viable cell concentration over time for a perfusion bioreactor controlling for viable cell concentration using a RAMAN probe.

Figure 16:
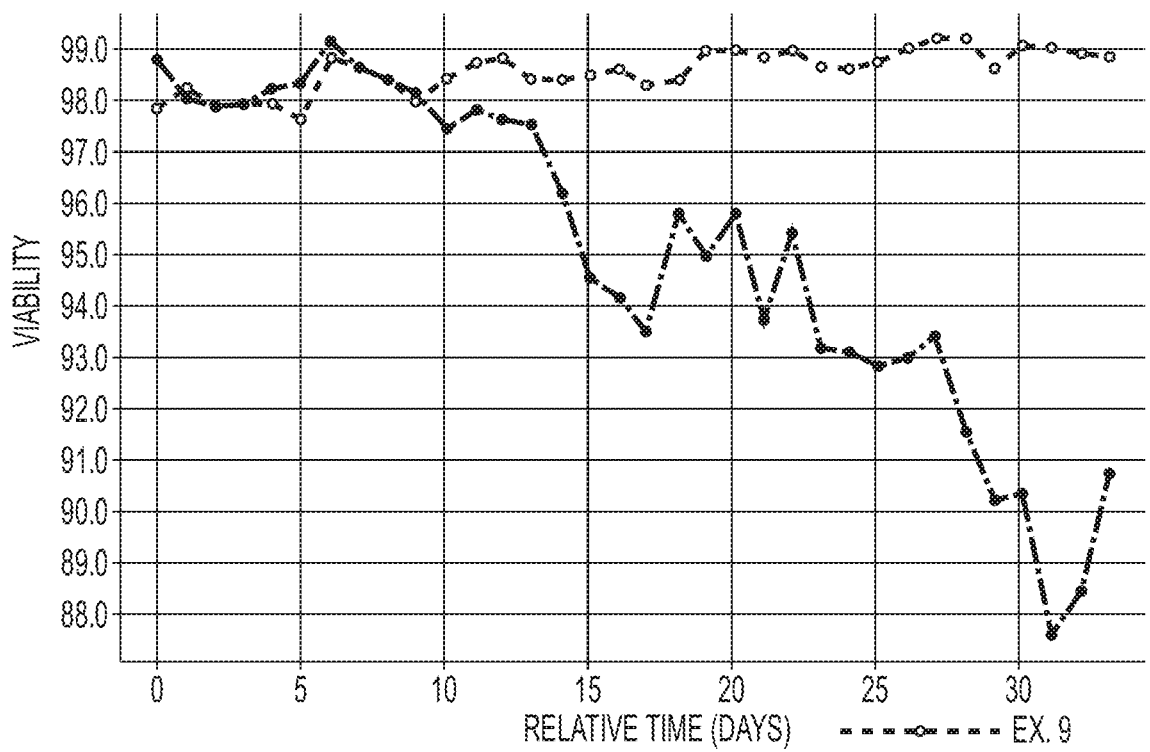

FIG. 16 is a graph showing cell viability over time in the perfusion bioreactor described in FIG. 15.

Figure 17:
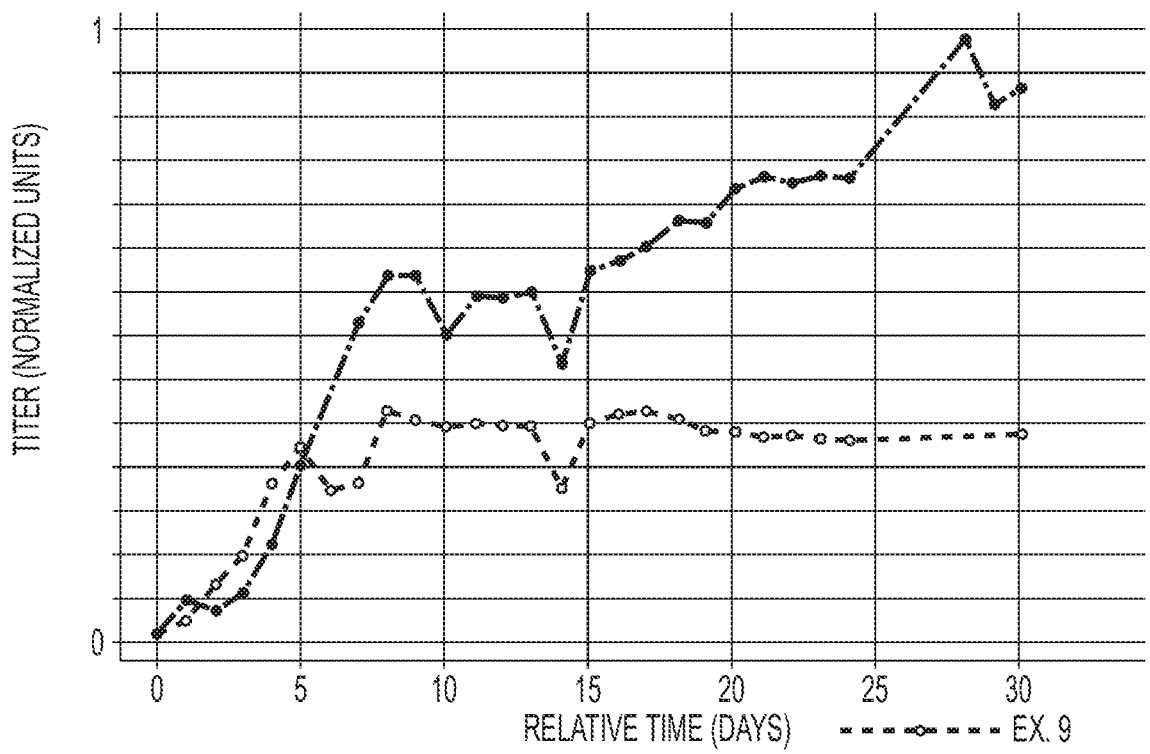

FIG. 17 is a graph showing normalized protein production (titer) over time in the perfusion bioreactor described in FIG. 15.

Figure 18:
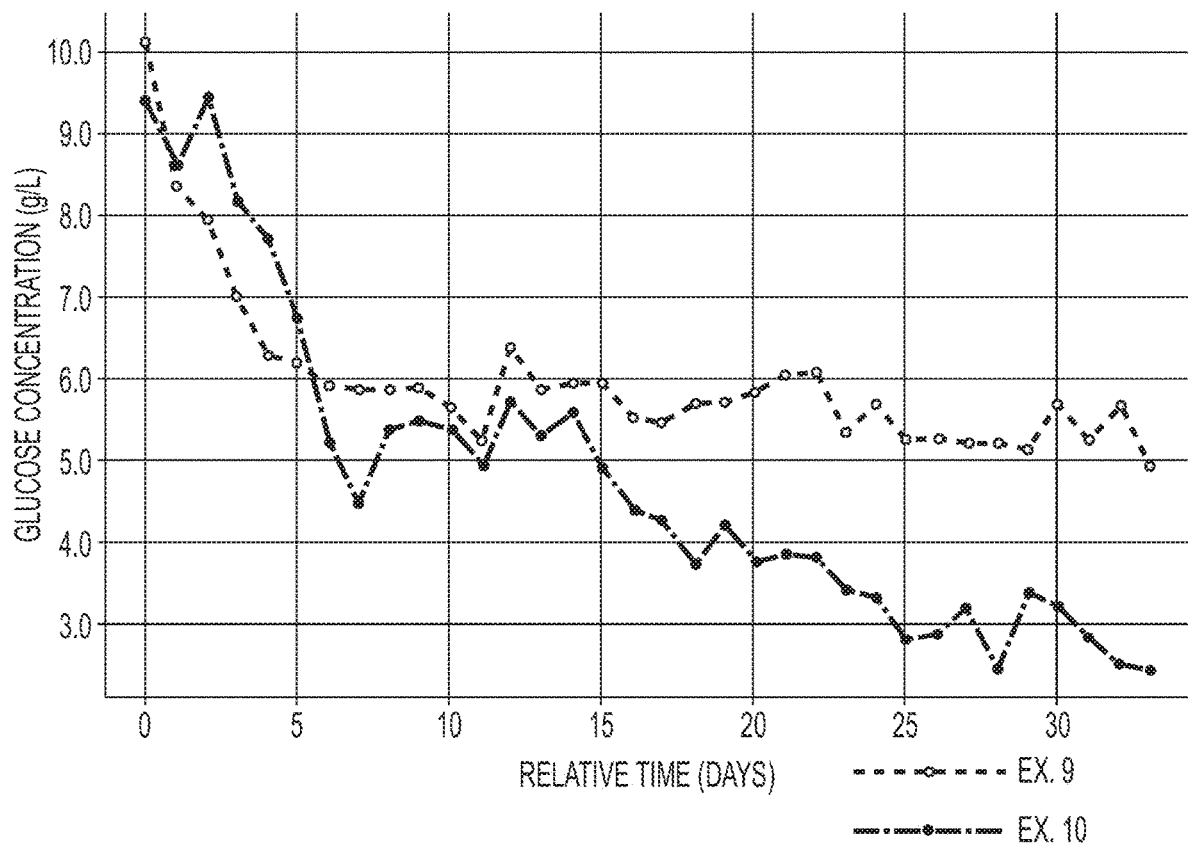

FIG. 18 is a graph showing glucose concentration over time in the perfusion bioreactor described in FIG. 15.

Figure 19:
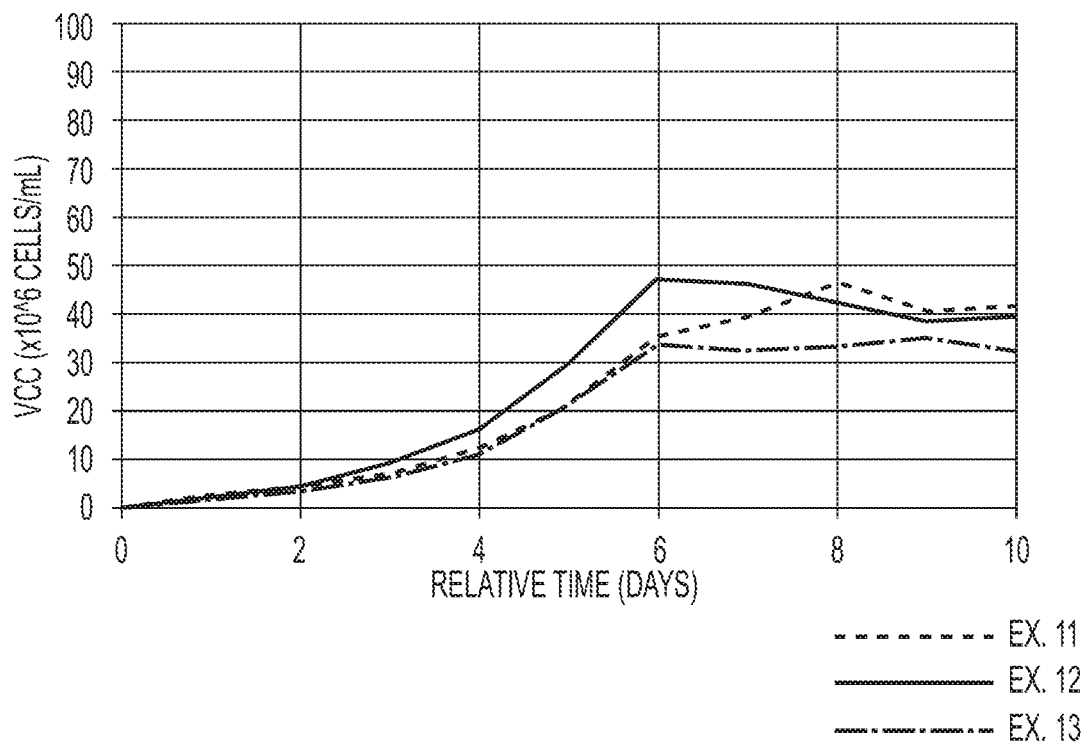

FIG. 19 is a graph showing viable cell concentration over time for perfusion bioreactors controlling for viable cell concentration using a RAMAN probe.

Figure 20:
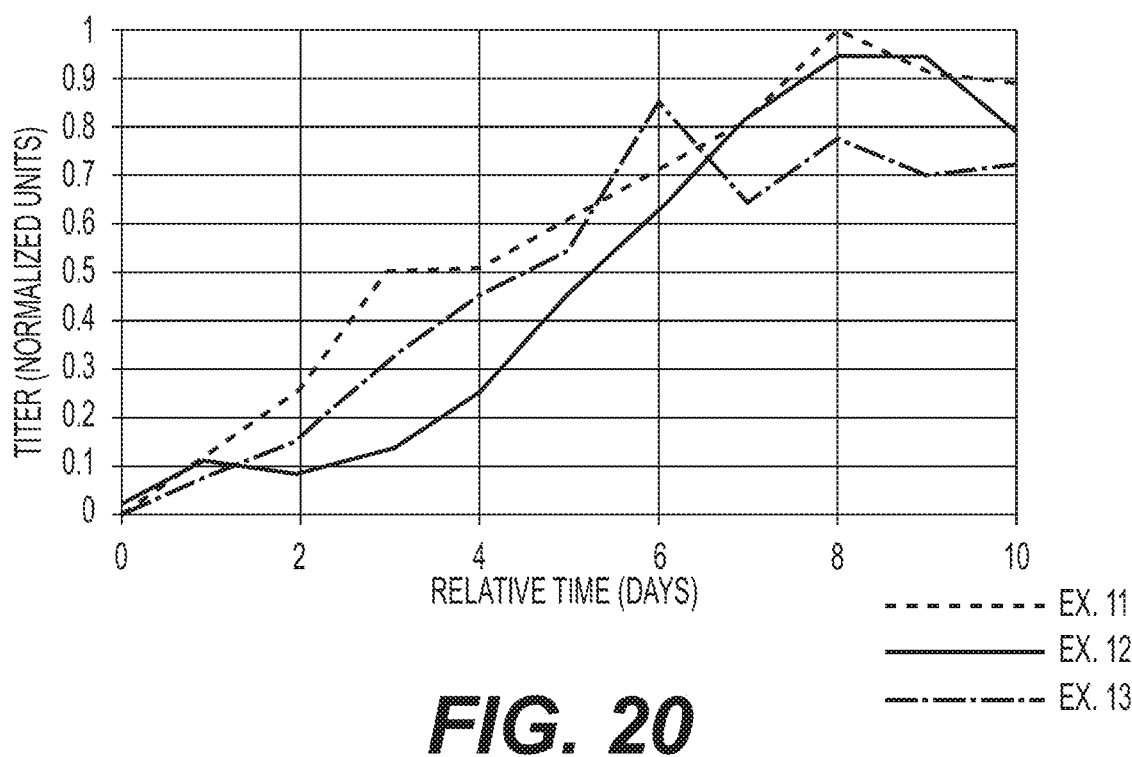

FIG. 20 is a graph showing normalized protein production (titer) over time in the perfusion bioreactors described in FIG. 19.

Figure 21:
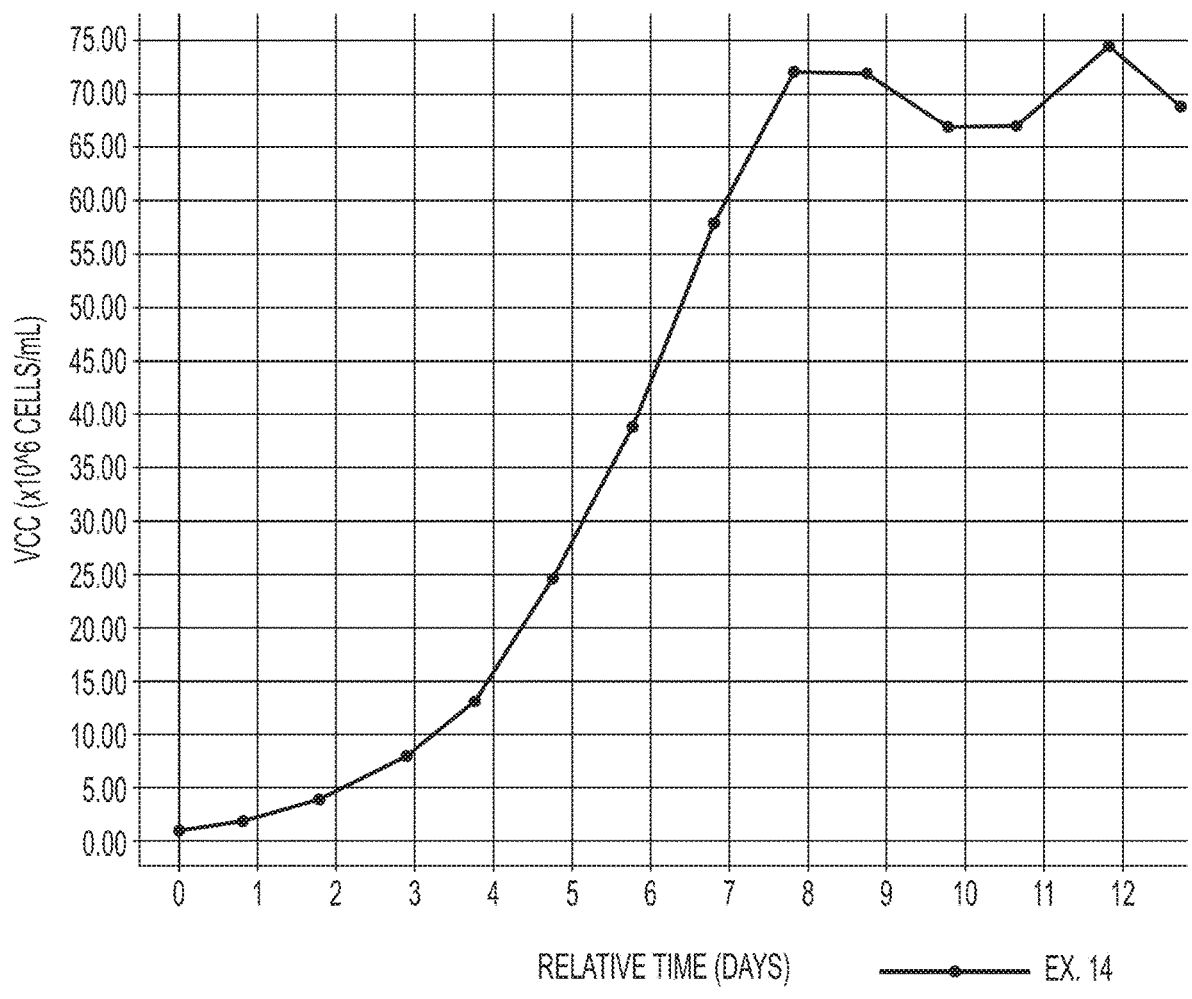

FIG. 21 is a graph showing viable cell concentration over time for a perfusion bioreactor controlling for viable cell concentration using a RAMAN probe.

Again, there are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

Notably, for simplicity and clarity of illustration, certain aspects of the figures depict the general structure and/or manner of construction of the various embodiments. Descriptions and details of well-known features and techniques may be omitted to avoid unnecessarily obscuring other features. Elements in the figures are not necessarily drawn to scale; the dimensions of some features may be exaggerated relative to other elements to improve understanding of the example embodiments. For example, one of ordinary skill in the art appreciates that the cross-sectional views are not drawn to scale and should not be viewed as representing proportional relationships between different components. The cross-sectional views are provided to help illustrate the various components of the depicted assembly, and to show their relative positioning to one another.

DETAILED DESCRIPTION

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated numeric value. Moreover, in the claims, values, limits, and/or ranges means the value, limit, and/or range ±10%.

The term "conduit" refers to a channel, tubing, connection, passageway, or the like, through which a fluid may travel. In one example, a conduit may include Bioprene thermoplastic tubing from Watson-Marlow.

"Batch culture" or "batch mode" refers to a unit (e.g., culturing vessel) that is filled with cells and with an initial working volume of cell culture medium that is never exchanged. In such a batch culture, all components for cell culturing are supplied to the culturing vessel at the start of the culturing process. The culture may run until the nutrients are exhausted or the waste products reach toxic levels, triggering apoptosis.

The phrase "fed-batch cell culture" or "fed-batch culture" refers to a batch culture wherein the animal cells and culture medium are supplied to the culturing vessel initially and additional culture nutrients are fed, either continuously or as discrete bolus additions, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" by the addition (or removal) of components to the vessel during culturing. Fed-batch culture can be further distinguished from perfusion culturing insofar as the media is not exchanged during the fed-batch process, whereas in perfusion culturing, all or some of the cells are retained in the culture by, e.g., using a filter or cell retention device, and culture medium is continuously or intermittently supplied while growth-inhibiting by-products are constantly or periodically removed from the culturing vessel. In a fed-batch process, which differs from a perfusion process, the culture continues until it is determined that maximum or an otherwise determined working volume and/or protein production is reached and then the fed-batch culture products are harvested.

Perfusion culture as a method for production of the protein of interest is also contemplated for use in the methods of the present disclosure. Perfusion cell culture methods for the production of a protein of interest or an antibody are known by one of ordinary skill in the art.

The term "cell" includes any cell that is suitable for expressing a recombinant nucleic acid sequence. Cells include those of prokaryotes and eukaryotes. Eukaryotic cells include, but are not limited to yeast and all mammalian cells (human and non-human), and cell fusions such as, for example, hybridomas or quadromas. In certain embodiments, the cell is a human, monkey, ape, hamster, rat or mouse cell. In other embodiments, the cell is selected from the following cells: CHO (e.g. CHO K1, DXB-11 CHO, Veggie-CHO), COS (e.g., COS-7), retinal cells, lymphocytes, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g., a PER. C6® cell). In some embodiments, the cell is a CHO cell. In other embodiments, the cell is a CHO K1 cell.

A "cell line" refers to a cell or cells that are derived from a particular lineage through serial passaging or subculturing of cells. The term "cells" is used interchangeably with "cell population."

Given the current state-of-the-art feeding strategies, CHO cells have achieved cell numbers such as greater than $10 \times 10^6$ cells/mL (after about one week) and titers of, for example, >2 g/L human IgG (harvested after about two weeks), numbers that are typical industrial values for CHO cell fed-batch cultures. See Kim, B J, et al., Biotechnol Bioeng. 2012 January; 109(1):137-45. Even more than 10 g/L production of antibody has been reported from CHO cells which have been well established as an important industrial mammalian cell line. See Omasa et al, Current Pharmaceutical Biotechnology, 2010, 11: 233-240.

The terms "cell culture medium" and "culture medium" refer to a nutrient solution used for growing mammalian cells that typically provides the necessary nutrients to enhance growth of the cells, such as a carbohydrate energy source, essential amino acids, trace elements, vitamins, etc. Cell culture medium may contain extracts, e.g., serum or peptones (hydrolysates), which supply raw materials that support cell growth. Media may contain yeast-derived or soy extracts, instead of animal-derived extracts. Chemically defined medium refers to a cell culture medium in which all of the chemical components are known. Chemically defined medium is entirely free of animal-derived components, such as serum- or animal-derived peptones. The medium also may be protein-free. "Fresh media" is media that has not yet been introduced into the cell culture and/or has not yet been utilized by cells of the cell culture. Fresh media may include generally high nutrient levels and little to no waste products. "Spent media" may refer to media that has been used by cells in the cell culture, and may generally include lower nutrient levels (as those nutrients may be utilized by cells in the cell culture) and higher waste levels than levels present in fresh media.

In a perfusion bioreactor, culture medium may be continuously removed from the cell culture and replaced with fresh medium. The constant addition of fresh medium while eliminating waste products may provide the cells in the cell culture with the nutrients they require to achieve high cell concentrations. Unlike the continually changing conditions during batch and fed-batch cultures, the perfusion method offers the means to achieve and maintain a culture in steady state. Typically, about one culture volume is exchanged per day and the cell concentration achieved in perfusion is typically two to more than ten times that achieved at the peak of batch or fed-batch culture. Replacement of nutrients and/or removal of apoptotic cells allows cell viability to be maintained long term at steady state. In a steady state production, protein (or other compounds of interest) quality attributes produced early in the batch may be substantially identical to protein (or other compounds of interest) quality attributes produced late in the batch. Protein may be evaluated based on various post-translational modifications such as glycoforms, charge heterogeneity, aggregation, and various measures of purity. The substantial identity of protein quality is not achievable in fed-batch reactors, as the cell culture conditions in such reactors are constantly changing.

Culture conditions in the bioreactor enable the cell culture to produce a protein of interest (POI), with the goal of providing consistent protein material. In some culture conditions of the cell culture, one or more process parameters may be selected from at least the group consisting of nutrient concentration, such as glucose concentration, glutamate concentration, and glutamine concentration; ammonia concentration; lactate concentration; total cell density; viable cell density; and protein attributes.

The bioreactor method allows for setting controls on the flow of various constituents such as media (including e.g. nutrients), protein, and cells in and out of the bioreactor. The bioreactor method includes removing cell-free spent media from the cell culture using a first output conduit at a first specified flow rate. The method includes removing cells from the cell culture using a second output conduit at a second specified flow rate. The method includes introducing one or both of fresh media or nutrients into the cell culture using an input conduit at a third specified flow rate. One or more of the first, second, and third specified flow rates are adjusted based on the RAMAN probe measurements of the bioreactor. One or more of the first, second, and third specified flow rates are adjusted based on the RAMAN probe measurements of the bioreactor to maintain the one or more of the process parameters within predetermined ranges. The first, second, and third specified flow rates are adjusted based on the RAMAN probe measurements of the bioreactor to maintain the third specified flow rate of the input conduit and the first and second specified flow rates of each of the output conduits within respective predetermined ranges.

Each of removing cell-free spent media, removing cells, and introducing one or both of fresh media or nutrients, is controlled by a respective pump. The bioreactor includes a filter configured to retain cells and allow fluid to pass through The methods and systems of the disclosure include a method of controlling the weight of the bioreactor, and its contents, to employ a consistent production process, amongst other reasons. The method includes measuring a weight of the bioreactor comprising the cell culture contents. In a further embodiment, the method employs controlling the weight of the bioreactor coupled to control of the flow rates, as described in connection with the conduits hereinabove. The method includes measuring a weight of the bioreactor with cell culture contents, wherein one or more of the first, second, and third specified flow rates are adjusted based on the measured weight. The first, second, and third specified flow rates are adjusted based on the measured weight to maintain the third specified flow rate of the input conduit and the first and second specified flow rates of each of the output conduits within respective predetermined ranges. The first, second, and/or third specified flow rates are adjusted to maintain the weight of the cell culture and bioreactor within a predetermined range. Measuring process parameters (PPs) of the cell culture within the bioreactor by the RAMAN probe occurs at least once per hour. The method is configured to maintain the cell culture at an average viable cell concentration of at least 30 million cells per mL for at least about 30 days at steady state. The bioreactor has a volume of at least 10 L, and the method is configured to maintain a weight of the bioreactor and cell culture within a 20 g range. The bioreactor has a volume of at least 10 L, and the method is configured to maintain a weight of the bioreactor with the cell culture within 0.1 percent of an initial weight of the bioreactor with the cell culture. When a process parameter deviates from a set point value within a respective desired range, one or more of removing cell-free media, removing cells, and introducing one or both of fresh media or nutrients, is adjusted to reduce the deviation. For example, at least two bioreactor volumes of spent media is removed through the first output conduit per day, or up to three bioreactor volumes of spent media is removed through the first output conduit per day.

The one or more process parameters also includes temperature of the cell culture and pH of the cell culture, and the temperature is maintained between 35 and 36 degrees C., and the pH is maintained between 6.85 and 7.15. In other embodiments, the pH is maintained between about 6.50 to about 7.50, from about 6.60 to about 7.40, from about 6.70 to about 7.40, from about 6.80 to about 7.30 from about 6.90 to about 7.20, from about 7.00 to about 7.10, at about 6.50, at about 6.55, at about 6.60, at about 6.65, at about 6.70, at about 6.75, at about 6.80, at about 6.85, at about 6.90, at about 6.95, at about 7.00, at about 7.05, at about 7.10, at about 7.15, at about 7.20, at about 7.25, at about 7.30, at about 7.35, at about 7.40, at about 7.45, or at about 7.50.

The one or more process parameters includes cell specific productivity, and the method is configured to maintain cells within the cell culture at a cell specific productivity of at least 15-25 pg/cell/day for at least 25-37 days.

The one or more process parameters includes glucose concentration, and the method is configured to maintain a glucose concentration between about 5 mM to about 85 mM, or about 1 g/L to about 15.5 g/L.

The one or more process parameters includes lactate concentration, and the method is configured to maintain a lactate concentration less than about 60 mM, or less than about 6 g/L.

The one or more process parameters includes ammonia concentration, and the method is configured to maintain an ammonia concentration less than about 15 mM.

The term "steady state" refers to maintaining the concentration of nutrients, process parameters, or the quality attributes in the cell culture at an unchanging, constant or stable level. It is understood that an unchanging, constant or stable level refers to a level within predetermined set points or predetermined set ranges. Set points, and therefore steady state levels, may be shifted during the time period of a production cell culture by an operator. Set points or steady state levels also may include set ranges of values, or thresholds.

The term "predetermined" may refer to a quantity or setpoint, the value of which is fixed or calculated manually by a user, or by a controller according to one or more algorithms.

Throughout the process of manufacturing a particular therapeutic protein product, product attributes or protein quality attributes in need of control may be identified based upon their potential quality impact, especially clinical impact. Relevant protein quality attributes may impact purity, safety and/or efficacy. Quality attributes refer to physical, chemical, biological, or microbiological property or characteristic of the drug product being produced that should be within an appropriate limit, range, or distribution to ensure the desired product (protein) quality. See, e.g., International Council for Harmonization (ICH) Q8 (R2) *Pharmaceutical Development* (ICH, August 2009). Quality attributes for protein products may include, but are not limited to, high molecular weight species, aggregates, charge variants, appearance, color, pH, potency, post-translational modifications (glycan content and distribution), conductivity, isoelectric point, charge heterogeneity, disulfide bond scrambling, free cysteine, host cell proteins, and may be considered attributes that have a high impact on the product quality. Certain process parameters are controlled within an appropriate limit, range or distribution during production culture for operational reliability and consistency during the manufacturing process. Process parameters may include initial cell density, initial cell viability, final cell viability, total protein (titer), viable cell count (VCC), nutrient concentration (glucose, phosphate, amino acids, etc.), ammonia, pH, lactate, and more. A drug product that is sensitive to a particular process parameter during the manufacturing process may cause changes in a protein attribute above or below a threshold for that particular attribute, and therefore requires proper control. As such, process parameters also includes process parameters whose variability may have an impact of greater than or equal to a defined threshold on any quality attribute listed above and therefore should be monitored or controlled to ensure the process produces material of the desired quality.

The terms "cell specific productivity", "cell specific rate" and the like, refer to the specific, e.g., per cell, or per measure of cell mass or volume, product expression rate. The cell specific productivity is measured in, for example, grams of protein produced per cell per day.

A bioreactor system 1 may include a bioreactor tank 10, a feed reservoir 28, a feed pump 30, a bleed pump 40, and a harvest pump 50. Bioreactor system 1 also may include an ATF pump 70, a bleed tank 80, and a harvest tank 90. Pumps 30, 40, 50, and 70, may be operatively coupled to a controller 200. In some examples, however, ATF pump 70 may be coupled to and controlled by a separate controller 102.

Bioreactor tank 10 may be a vat, barrel, vessel, flask, or other suitable container, sized for numerous operation scales. For example, the volume of bioreactor tank 10 may be from about 1 L to about 20,000 L, from about 5 L to about 10,000 L, from about 10 L to about 1,000 L, from about 20 L to about 100 L, about 50 L, at least about 1 L, at least about 10 L, at least about 50 L, at least about 100 L, at least about 200 L, at least about 500 L, at least about 1,000 L, at least about 10,000 L, less than about 20,000 L, less than about 10,000 L, less than about 1,000 L, less than about 500 L, less than about 200 L, or less than about 100 L. In other embodiments, bioreactor tank 10 has a volume of at least 2 L, at least 3 L, at least 10 L, at least 35 L, or at least 50 L, or more. Bioreactor tank 10 may be made from metal (e.g., steel or stainless steel), a metal alloy, glass, and/or a polymer (e.g., a disposable, single-use bioreactor).

Pumps 30, 40, and 50 may include any suitable pumps, such as, e.g., peristaltic pumps, diaphragm pumps, piston pumps, motorized pumps, or the like. In one example, pumps 30, 40, and 50 may be substantially identical to one another. In another example, one or more of pumps 30, 40, and 50 may be different than the other(s). In yet another example, pump 70 may be similar to any one of pumps 30, 40, and 50. Feed reservoir 28 may include any suitable source of nutrient feed for bioreactor tank 10, and the nutrient feed may be directed to bioreactor tank 10 via feed pump 30 via a suitable conduit. The nutrient feed (growth media) may include a carbon source (e.g., glucose), water, salt, a source of amino acids, and/or other nutrients.

A cap 12 may cover a top of bioreactor tank 10, and various components and instruments may extend through cap 12 into an interior of bioreactor tank 10. For example, an aerator 14, an agitator 16, a RAMAN probe 18, a conduit 20, and a conduit 22 may extend through cap 12. However, it is contemplated that any or all of aerator 14, agitator 16, RAMAN probe 18, conduit 20, and conduit 22 may be operatively coupled to bioreactor tank 10 in any other suitable manner, such as, e.g., through a side surface of bioreactor tank 10.

Aerator 14 may be a sparger configured to provide oxygen and/or other gases to a cell culture within bioreactor tank 10. Aerator 14 may be coupled to a source of oxygen or other gas, and may direct the gas to the cell culture so that the gas bubbles in the cell culture, thereby aerating the cell culture. In some examples, a microsparger may be used in combination with a drilled tube sparger.

Agitator 16 may be any suitable agitator configured to mix the cell culture within bioreactor tank 10. Agitator 16 can be top-driven or bottom-driven by mechanical and/or magnetic mechanisms. A bottom driven agitator may be desired in some instances because it may free up space in cap 12 for sensing instrumentation, such as, e.g., temperature, pH, dissolved oxygen, foam, carbon dioxide, and other sensors, as well as inlet ports for acid, alkali, foam, fresh media inlet, and exit ports. Agitator 16 may include a radial agitator, an axial agitator, a Rushton impeller, a pitched-blade impeller, a marine-blade impeller, or the like.

Raman probe 18 may be, for example, a fiber-optic Raman probe in, e.g., a stainless steel enclosure, and having a transparent, e.g., sapphire or glass, window. Raman probe 18 may be configured to allow for Raman sampling of cell culture 2. Raman probe 18 may be configured to shine a monochromatic light (e.g., a laser at 785 nm or another suitable wavelength) on cell culture 2 and detect scattered light from cell culture 2.

Raman spectroscopy is a form of vibrational spectroscopy that provides information about molecular vibrations that can be used by inserting a Raman probe in situ for sample identification and quantitation. In some embodiments, the monitoring of the process variables is performed using in situ Raman spectroscopy. In situ Raman analysis is a method of analyzing a sample in its original location without having to extract a portion of the sample for analysis in a Raman spectrometer. In situ Raman analysis is advantageous in that the Raman spectroscopy analyzers are noninvasive, which reduces the risk of contamination, and nondestructive with no impact to cell culture viability or protein quality. The in situ Raman analysis can provide real-time assessments of one or more process variables in cell cultures. Manufacturers of Raman probes include, but are not limited to, tech5usa, Anton Paar, InPhotonics, Kaiser Optical Systems, Inc. and FiberTech Optica.

Bioreactor tank 10 may be coupled to a filter system 100 having a hollow fiber filter therein. The hollow filter membrane (e.g., polysulfone) may include one or more tubular membranes having an internal diameter from about 0.3 mm to about 6.0 mm, from about 0.5 mm to about 3.0 mm, from about 0.5 mm to about 2.0 mm, greater than about 0.3 mm, greater than about 0.5 mm, less than about 6.0 mm, less than about 3.0 mm, or less than about 2.0 mm. A mesh material in the membrane may be chosen such that the size of pores in the mesh is close to the diameter of the cells from cell culture 2, helping to ensure a high retention of cells while allowing cell debris and spent media to pass through the filter. In one example, the mesh pore size is from about 0.2 μm to about 30 μm, although other suitable ranges and values also are contemplated. Protein, or other biological products of interest, can be perfused or retained based on filter pore size (e.g., 0.2 μm or 50 kD).

Fluid from bioreactor tank 10 may be delivered to filter system 100 via conduit 20 and pump 70. Pump 70 may be reversible to allow fluid to flow from filter system 100 back to bioreactor tank 10. Filter system 100 may operate under alternating tangential flow. In one example, alternating tangential flow may mean that there is one flow in the same direction as (e.g., tangential to) the membrane surfaces of the hollow fibers, which flow is going back and forth, and that there is another flow in a direction substantially perpendicular to said filter surface. Alternating tangential flow can be achieved using one pump (e.g., pump 70) to circulate the cell culture over a filter module comprising hollow fibers and another pump (e.g., pump 50) to remove the liquid having a lower cell density prior to the filter separation. Alternating tangential flow may help prevent fouling and shear issues typical of other cell retention mechanisms.

Alternatively, other filtration mechanisms (including membrane filtration mechanisms) may be utilized, such as, for example, ultrafiltration, microfiltration, and tangential flow filtration.

Bleed pump 40 may be configured to remove cells from bioreactor tank 10 via conduit 22. Conduit 22 may be a dip tube selected to avoid cell aggregation and clogging (which, e.g., may result if conduit 22 is too narrow relative to the viscosity of culture 2). Conduit 22 may include a thermoplastic elastomer tubing (e.g., bioprene). Bleed pump 40 may be controlled via, e.g., processor 200. A cell bleed via bleed pump 40 may remove cells from cell culture 2 within bioreactor tank 10. The cell bleed rate (controlled by the output of bleed pump 40 and controller 200) may be determined based on the growth rate of cells in cell culture 2. To maintain a steady cell density in cell culture 2, it may be desirable to have the bleed rate and the cell growth rate approximately or substantially equal to one another. In some examples, if there is a significant volume of cell culture 2 being removed from the cell bleed with valuable product, then the bleed can be collected and processed to recover the product.

Bioreactor tank 10 may be positioned on a scale 110 configured to measure a weight of bioreactor tank 10 and cell culture 2. Scale 110 may be coupled to controller 200, and may continuously send a weight of bioreactor tank 10 and cell culture 2 to controller 200. In some examples, at least a portion of filter system 100, including e.g., a filter housing and hollow membrane filter therein, also may be positioned on scale 110. Scale 110 may be any suitable scale or load cell configured to measure a weight of components resting on the scale.

Referring to FIGS. 1 and 2, controller 200 may be configured to receive data from Raman probe 18, scale 110, and other sensors, and may be configured to control the rate of fluid flow through one or more of feed pump 30, bleed pump 40, and harvest pump 50 based on the data.

Controller 200 may be configured to receive raw spectral data from Raman probe 18 to determine process parameters such as, e.g., glucose concentration, glutamine concentration, glutamate concentration, ammonia concentration, lactate concentration, total cell density, titer, and viable cell density. Controller 200 may use these determined process parameters to establish a feedback loop to adjust one or more of the fluid flow through feed pump 30, bleed pump 40, and harvest pump 50. That is, controller 200 may establish set points for one or more of glucose concentration (e.g., from about 5 mM to about 85 mM, or from about 0.5 g/L to about 15.5 g/L, from about 1 g/L to about 15.5 g/L, from about 0.5 g/L to about 8 g/L, from about 2 g/L to about 6 g/L, or from about 3 g/L to about 5 g/L), glutamine concentration (e.g., less than about 8 mM, less than about 7 mM, less than about 6 mM, less than about 5 mM, or less than about 4 mM), glutamate concentration (e.g., less than about 5 mM, less than about 4 mM, less than about 3 mM, less than about 2 mM, or less than about 1 mM), ammonia concentration (e.g., less than about 15 mM, less than about 12 mM, less than about 10 mM, less than about 9 mM, less than about 8 mM, less than about 7 mM, less than about 6 mM), lactate concentration (e.g., less than about 6 g/L, less than about 5 g/L, less than about 4 g/L, less than about 3 g/L, less than about 2 g/L, or less than about 1 g/L), total cell density (e.g., greater than about 30 MM, greater than about 35 MM, greater than about 40 MM, greater than about 45 MM, greater than about 50 MM, greater than about 55 MM, greater than about 60 MM, or greater than about 65 MM), and viable cell density (e.g., at least 30 million cells per mL, at least 35 million cells per mL, at least 50 million cells per mL, or at least 75 million cells per mL), and compare determined values (based on the Raman spectra from Raman probe 18) to their respective set points.

Controller 200 may utilize a negative feedback loop to correct any difference between a set point value (or a set range of values) and a determined value. For example, should a determined glucose concentration be greater than the set point glucose concentration, controller 200 may, e.g., decrease an output of feed pump 30, decrease an output of bleed pump 40, and/or increase an output of harvest pump 50 in order to help reduce the glucose concentration; or controller 200 may decrease an output of feed pump 30 and decrease an output of harvest pump 50. For example, should a determined glutamine concentration be greater than the set point glutamine concentration, controller 200 may, e.g., decrease an output of feed pump 30, decrease an output of bleed pump 40, and/or increase an output of harvest pump 50 in order to help reduce the glutamine concentration; or controller 200 may decrease an output of feed pump 30 and decrease an output of harvest pump 50. For example, should a determined glutamate concentration be greater than the set point glutamate concentration, controller 200 may, e.g., decrease an output of feed pump 30, decrease an output of bleed pump 40, and/or increase an output of harvest pump 50 in order to help reduce the glutamate concentration; or controller 200 may decrease an output of feed pump 30 and decrease an output of harvest pump 50. For example, should a determined ammonia concentration be greater than the set point ammonia concentration, controller 200 may, e.g., decrease an output of feed pump 30, increase an output of bleed pump 40, and/or decrease an output of harvest pump 50 in order to help reduce the ammonia concentration; or controller 200 may increase an output of feed pump 30 and increase an output of harvest pump 50. For example, should a determined lactate concentration be greater than the set point lactate concentration, controller 200 may, e.g., increase an output of feed pump 30, decrease an output of bleed pump 40, and/or increase an output of harvest pump 50 in order to help reduce the lactate concentration; or controller 200 may decrease an output of feed pump 30 and decrease an output of harvest pump 50. For example, should a determined total cell density be greater than the set point total cell density, controller 200 may, e.g., decrease an output of feed pump 30, increase an output of bleed pump 40, and/or decrease an output of harvest pump 50 in order to help reduce the total cell density; or controller 200 may decrease an output of feed pump 30 and decrease an output of harvest pump 50. For example, should a determined viable cell density be greater than the set point viable cell density, controller 200 may, e.g., decrease an output of feed pump 30, increase an output of bleed pump 40, and/or decrease an output of harvest pump 50 in order to help reduce the viable cell density; or controller 200 may decrease an output of feed pump 30 and decrease an output of harvest pump 50.

For example, should a determined glucose concentration be lower than the set point glutamine concentration, controller 200 may, e.g., increase an output of feed pump 30, increase an output of bleed pump 40, and/or decrease an output of harvest pump 50 in order to help increase the glucose concentration; or controller 200 may increase an output of feed pump 30 and increase an output of harvest pump 50. For example, should a determined glutamine concentration be lower than the set point glutamine concentration, controller 200 may, e.g., increase an output of feed pump 30, increase an output of bleed pump 40, and/or decrease an output of harvest pump 50 in order to help increase the glutamine concentration; or controller 200 may increase an output of feed pump 30 and increase an output of harvest pump 50. For example, should a determined glutamate concentration be lower than the set point glutamate concentration, controller 200 may, e.g., increase an output of feed pump 30, increase an output of bleed pump 40, and/or decrease an output of harvest pump 50 in order to help increase the glutamate concentration; or controller 200 may increase an output of feed pump 30 and increase an output of harvest pump 50. For example, should a determined lactate concentration be lower than the set point lactate concentration, controller 200 may, e.g., increase an output of feed pump 30, increase an output of bleed pump 40, and/or decrease an output of harvest pump 50 in order to help increase the lactate concentration; or controller 200 may increase an output of feed pump 30 and increase an output of harvest pump 50. For example, should a determined total cell density be lower than the set point total cell density, controller 200 may, e.g., increase an output of feed pump 30, decrease an output of bleed pump 40, and/or increase an output of harvest pump 50 in order to help increase the total cell density; or controller 200 may increase an output of feed pump 30 and increase an output of harvest pump 50. For example, should a determined viable cell density be lower than the set point viable cell density, controller 200 may, e.g., increase an output of feed pump 30, decrease an output of bleed pump 40, and/or increase an output of harvest pump 50 in order to help increase the viable cell density; or controller 200 may increase an output of feed pump 30 and increase an output of harvest pump 50.

However, the total perfusion through the system is maintained at a given setpoint (perfusion rate will not vary based on concentrations within the reactor). Controller 200 may similarly control bioreactor weight (and weight of cell culture 2) using a negative feedback loop.

It should be noted that the addition or subtraction of various nutrients input into the reactor may be coupled with a corresponding change to other inputs to ensure that the total mass and/or volume of material input into the reactor stays the same. That is, because perfusion rate is maintained at a constant, the increase of one nutrient, e.g., a glucose solution, glutamine, glutamate, or the like, may be accompanied by a corresponding mass or volume decrease in the primary nutrient feed stream.

In one embodiment, the system may include at least two feedback loops—one for weight control and one for control of process parameters (e.g., VCC, glucose, glutamine, glutamate, ammonia, lactate, etc.) In one example, the various input and output pumps are not controlled by competing loops. For example, a perfusion rate may be set (e.g., 20 L/day), after which RAMAN probe 18 measures one or more culture values, and controller 200 assesses steps to take based on the measurements from RAMAN probe 18. If controller 200 determines that, e.g., VCC is too high, controller 200 may begin removing cells via bleed pump 40, and the flow rate of harvest pump 50 may be decreased concurrently so that the total volume through the system remains constant. Additional steps to be taken by controller 200 when it is sensed that other process parameters are too high or too low (e.g., glucose, glutamine, glutamate, ammonia, lactate, and total cell density) are described above.

A second feed pump could be added to add glucose, lactose, glutamine, glutamate, etc. In either an alternative embodiment or in addition, the bleed could be adjusted to react to increasing ammonia by removing cells as well.

Controller 200 may be disposed in a headless computer system (e.g., a system without a monitor, keyboard, and mouse). Thus, controller 200 may be located in a server that is controlled via a network connection or some other connection, such as, e.g., a serial connection. Controller 200 may be cloned on one or more redundant servers in case of failure of one or more of the servers.

Controller 200 may be configured to apply Kalman filtering, e.g., linear quadratic estimation (LQE) to Raman spectral data from Raman probe 18. The Kalman filtering may include applying an algorithm to the spectral data that uses a series of measurements over time to produce estimates of unknown variables that tend to be more accurate than those based on a single measurement alone. Thus, the determined process parameters may be based on filtered models. It is contemplated that other types of filtering also may be used by controller 200 to process the spectral data from Raman probe 18.

Controller 200 may include or may be otherwise coupled to a PI (process information) historian. The PI historian may be an application with a time-series database that can record data from process control systems. The PI historian may enable users to record, analyze, and monitor real-time information. Controller 200 may store, e.g., weight values from scale 110, spectral data from Raman probe 18, and pump rates of feed pump 30, bleed pump 40, and harvest pump 50, in the PI historian.

FIG. 3 illustrates a method 300 according to the disclosure. One or more steps of method 300 may be performed out of order, performed simultaneously with other steps, or eliminated altogether. Method 300 may start at step 302, where bioreactor system 1 may be assembled, and cell culture 2 may be provided within bioreactor tank 10 and inoculated with a cell line. Method 300 then may proceed to step 304, where process parameters of cell culture 2 are measured within the bioreactor by Raman probe 18 and/or by additional or other sensors. The process parameters may include any of the aforementioned parameters determined from the Raman spectral data obtained by Raman probe 18. Method 300 may proceed to step 306, where a weight of bioreactor tank 10 (including cell culture 2 within) is measured by scale 110 and provided to processor 200.

From step 306, method 300 may proceed to step 308, where cell-free spent media from cell culture 2 is removed at a first specified rate by activating pump 70 to withdraw cell culture (media plus cells) from bioreactor tank 10 via conduit 20, and also by activating harvest pump 50 to withdraw solution from filter system 100. From step 308, method 300 may proceed to step 310, where cells may be removed from the cell culture using output conduit 22 at a second specified rate by bleed pump 40. From step 310, method 300 may proceed to step 312, wherein one or both of fresh media and nutrients may be introduced into the cell culture at a third specified rate using an input conduit and feed pump 30 in a manner that keeps the total input of media and nutrients equal to the combined output of bleed pump 40 and harvest pump 50. A specified rate may be a rate setpoint or range of rates at which a pump is operated and/or maintained. The specified rates may be determined by controller 200.

It is contemplated that each of steps 302 through 312 may occur in any order, and in some instances, may be occurring simultaneously in real-time via multiple feedback loops run by controller 200.

Steps 308, 310, and 312 may be controlled by controller 200 based on data received from Raman probe 18 at step 304, and from scale 110 at step 306. The weight of bioreactor tank 10 (plus cell culture 2 contained therein) may be controlled via a PID (proportional-integral-derivative) loop. Additionally, controller 200 may be configured to analyze the Raman spectra obtained from Raman probe 18 to determine one or more process parameters including, e.g., glucose concentration, glutamine concentration, glutamate concentration, ammonia concentration, lactate concentration, total cell density, and viable cell density. Each of these variables also may be controlled by a negative feedback loop.

Examples of the present disclosure may provide elegant, flexible, and inexpensive solutions to existing control solutions, and may have relatively few data gaps. Control strategies of the present disclosure may exhibit consistent bioreactor level control. For example, level variance was decreased from +/−0.5 L/day to +/−0.01 L/day using control systems of the present disclosure. Weight variance improvements have also been achieved, for example a decrease from 5-10% weight variance using other systems such as volumetric calibration to 0.1-0.5% error using control systems disclosed herein. The improvement may be at least partly due to changing the system from a volumetric calibration of pumps to a software controlled version based on weight and other parameters. Furthermore, control systems of the present disclosure may be fully integrated with process information (PI) alarms (e.g., email alerts), and can be accessed and shutdown remotely. Furthermore, systems and methods of the present disclosure may provide more repeatable and reliable results than prior systems and methods.

Example 1 (FIGS. 4 and 5)

The experiments described in Example 1 compare a perfusion bioreactor with a fed-batch bioreactor, and show higher attained viable cell concentrations and cell specific productivity in the perfusion bioreactor versus the fed-batch bioreactor.

In one experiment, a 15 L capacity bioreactor was cultured using cell lines and medium. The bioreactor set points included temperature (35.5 degrees Celsius), agitation (250 RPM), pH (controlled using $CO_2$ and sodium bicarbonate) (from 6.85 to 7.15), and working volume (11 L). An ATF4 Cell Retention Device, equipped with a 0.2 µm hollow fiber filter was coupled to the bioreactor. The hollow fiber filter retained cells but allowed proteins and nutrients to pass through. Two reactor volumes (or 22 L of medium) were passed through the filter every 24 hours.

Both the bioreactor and the ATF were positioned on a scale. The weight of the bioreactor, cell culture, and ATF were transmitted via Ethernet connection to a computer running control software. The weight was compared against a set point (11.0 kg, e.g., the working volume of the bioreactor), and a PID controller (designed in MATLAB, but executed via the control software SynTQ) determined whether or not to engage a feed pump. A harvest pump was set at a constant rate equivalent to the desired perfusion rate (two reactor volumes per day). The feed pump and the perfusion pump were automatically controlled using SynTQ software, which broadcast an OPC signal to a Kepware server. The Kepware server broadcast this signal across an Ethernet connection to a MODBUS Analog Output Module, which converted the digital value to a physical milliamp output between 4 and 20 mA.

Using this system, bioreactor weight could be controlled to within 10 g of the initial 11 kg weight (0.09%). Before this system was implemented, it was not possible to control bioreactor weight to within more than 0.5 kg (4.54%) overnight in the bioreactor. Within the same system, a Kaiser Optical Raman probe was used to capture Raman spectra from the cell culture. The controller utilized models that were developed in previous batches to predict cell count, glucose, lactate, ammonia, and other nutrient concentrations. The RAMAN probe captures thousands of different spectra that are then analyzed in a computer program, e.g., SIMCA. Using multiple component analysis, and offline data for the given parameter, the program creates a model across all the probe readings. This SIMCA model is then uploaded into SynTQ and is accessed real time each time the probe takes a reading (e.g., every 15 min to 45 min).

Control of various nutrients with the Raman probe allows for higher productivity of cell lines, increased viabilities over long term cell culture, and improved quality of multiple aspects of the protein.

FIG. 4 illustrates that the maximum viable cell concentration in a perfusion bioreactor (Exhibit "Ex." 1) according to the disclosure on day 37 of a batch, which is roughly double the maximum viable cell concentration of an equivalent sized fed-batch reactor at day seven of a batch (Ex. 2). The fact that the maximum viable cell concentration was achieved on day 37 (as opposed to day 6 in the fed-batch bioreactor), shows the robustness and longevity of the perfusion bioreactor process.

FIG. 5 shows cell specific productivity (cSP) for days 12-25 of a perfusion batch process (Ex. 1) against cSP for days 1-12 of a fed-batch process (Ex. 2). Similar productivities were achieved on days 25-37 of the perfusion batch.

A perfusion rate of three reactor volumes per day was required to increase VCC past $50 \times 10^6$ cells/mL in a perfusion batch, which may be commercially prohibitive in many cases.

Medium optimization using a "push-to-low" strategy should decrease perfusion rate needed. For instance, cells may be grown to $20 \times 10^6$ cells/mL, and kept at a steady state. The perfusion rate may be set to two reactor volumes/day for five days. On day five, the perfusion rate may be decreased to 1.5 reactor volumes/day. If the cells are sustained, the perfusion rate may be decreased to one reactor volume/day after 5 days. Once the cells start to die, amino acid analysis or other analysis may be used to determine how to better fortify the medium, e.g. supplement with nutrients or adjust nutrient concentration in the media. In one non-limiting example, the strategy is described in "The Push to Low Approach for Optimization of High Density Perfusion Cultures of Animal Cells" by Bayer et al. Adv. BioChem. Engin./Biotechnol. 2006, 101: 75-98.

NOVA Flex data may be obtained, where an offline reading is taken by analyzing a sample. Using previous NOVA data, a RAMAN model may be built and, at that point, a probe can be put into the reactor and the model can provide VCC data every 15 to 45 minutes, every second, every minute, every 2 minutes, every 3 minutes, every 4 minutes, every 5 minutes, every 10 minutes, every 15 minutes, every 20 minutes, every 25 minutes, every 30 minutes, every 35 minutes, every 40 minutes, every 45 minutes, every 50 minutes, every 55 minutes, every hour, every 2 hours, every 3 hours, every 4 hours, every 5 hours, or every 6 hours, instead of once daily and requiring manual sampling like with NOVA. FIG. 5 shows day 20 of a given run. The first 20 days of the run were used to gather NOVA data, which were used to create a RAMAN model for later portions of the run.

In the following examples, the following are general ranges for certain process parameters: pH: 6.85-7.40, dissolved oxygen: 30-60%, 35-55%, 40-50%, or 45%, temperature: 34-37.5° C., and agitation: 150-300 RPM, 175-275 RPM, 200-250 RPM, or 225 RPM at benchtop.

Example 2 (FIGS. 6-8)

The experiments described in example 2 show data for a perfusion bioreactor having no control for VCC growth or glucose. VCC was observed to peak at day 7 as the cells quickly grew to a large cell density then quickly declined through day 11 as they depleted the nutrients within the media (FIG. 6). Weight-only control was not sufficient to achieve steady-state of VCC.

Glucose also was not controlled during the perfusion run. Since the culture relied on glucose in the media during the perfusion run to feed the cells, this subsequently led to cell death during the culture. As the cells grew, glucose steadily declined although media was being consistently fed (FIG. 7). The spike in glucose detection occurring after day 10 was due to complete cell death and therefore no consumption of glucose, as can be seen when monitoring cell viability, represented in FIG. 8.

In this experiment, a 15 L benchtop bioreactor was inoculated with a given concentration of Chinese hamster ovary (CHO) cells producing mAb1. The cells were cultured at a specific dissolved oxygen, temperature, agitation, and pH that were held constant for the duration of the run. The cells also were provided fresh medium and nutrients in the form of the perfusion feed at a rate of two times the reactor volume per day. The reactor volume was held constant by adding the same amount of feed to the reactor that was being removed in the perfusate using the Repligen XCell ATF4 System. This was achieved by monitoring the weight of the bioreactor system and using a computer-aided feedback loop control system to maintain a weight within 0.05 kg of a given target weight. Neither RAMAN control nor bleed control was provided to control VCC or any other bioreactor parameter during this perfusion production run.

In an analogous experiment (not depicted in the figures), where the flow rate also was set to two bioreactors per day media feed, yet weight was not monitored, the variability of the pumps could not be adequately controlled.

In this analogous perfusion experiment, the feed pump and perfusate pump were set to equivalent flow rates (determined by volumetric calibration of the pumps). This method could not provide flow rates that were accurate enough to match each other, and overnight (for example, a period of time where the bioreactor was not actively monitored), the feed pump added more media to the reactor than the perfusate pump was able to remove. This resulted in the reactor overflowing and subsequent loss of the culture.

Example 3 (FIGS. 9-12)

The experiment described in example 3 show data for a perfusion bioreactor with VCC control. VCC control (FIG. 9) led to a consistent steady state of viability (FIG. 10), protein production (FIG. 11), and nutrients (FIG. 12).

In this experiment, a 15 L benchtop bioreactor was inoculated with a given concentration of CHO Cells producing mAb2. The cells were cultured at a specific dissolved oxygen, temperature, agitation, and pH that were held constant for the duration of the run. The cells also were provided fresh medium and nutrients in the form of the perfusion feed at a rate of two times the reactor volume per day. The reactor volume was held constant by adding the same amount of feed to the reactor that was being removed in the perfusate using the ATF4 system. This was achieved by monitoring the weight of the system and using a computer control system to maintain a weight within plus or minus 0.05 kg of a given target. RAMAN control was not used for this run, and the bleed rate of the pump was set manually after sampling VCC. This process required multiple samples and the bleed rate had to be adjusted multiple times a day.

VCC was controlled during the perfusion production culture, with a target VCC of $42.5 \times 10^6$ cells/mL ($40\text{-}45 \times 10^6$ cells/mL). Accordingly, if VCC rose above the target, then the bleed rate was increased, and if VCC fell below the target, then the bleed rate was decreased.

Example 4 (FIGS. 13 and 14)

The experiments in this example compare a perfusion culture method (FIG. 14) with a fed-batch culture method (FIG. 13). The perfusion culture method was able to achieve approximately four-fold maximum cell count compared to a fed-batch cell culture method for the same protein under analogous conditions (FIG. 13). The fed-batch culture was performed at the pilot scale, while the perfusion experiment took place at the bench scale (15 L). Agitation and aeration strategy were scaled down to the bench scale using a power per unit volume approach for agitation and volume by volume match strategy for aeration.

The perfusion culture method was able to produce 3.5 times the amount of protein compared to that produced in the fed-batch reactor in the same amount of time (FIG. 14).

A perfusion culture method was performed by providing a 15 L benchtop bioreactor inoculated with a given concentration of CHO Cells producing mAb2 (Exs. 5 and 7). The cells were cultured at a specific dissolved oxygen, temperature, agitation, and pH that was held constant for the duration of the run. The cells also were provided fresh medium and nutrients in the form of the perfusion feed at a rate of two times the reactor volume per day. The medium in this run was supplemented with increased concentrations of vital nutrients, compared to previous experiments, so that the cells could be pushed to higher cell densities during a perfusion run. The reactor volume was held constant by using the weight control system to maintain a weight within 0.05 kg of a given target. Neither RAMAN control nor any bleed control was provided during the perfusion production run.

The fed-batch cell culture (Exs. 6 and 8) was performed under analogous conditions (dissolved oxygen, temperature, agitation, and pH).

Example 5 (FIGS. 15-18)

The experiment described in FIGS. 15-18 show the beneficial results of viability, glucose, and titer, as well as VCC, maintained at steady state for longer than 30 days with this perfusion system (see, e.g., FIGS. 15-18).

A perfusion culture method with RAMAN, bleed, and weight control was performed by providing a 15 L benchtop bioreactor inoculated with a given concentration of CHO Cells producing mAb2. The cells were cultured at a specific dissolved oxygen, temperature, agitation, and pH range that were held constant for the duration of the run. The cells also were provided fresh medium and nutrients in the form of the perfusion feed at a rate of two times the reactor volume per day. The medium in this run was supplemented with increased concentrations of vital nutrients (compared to Examples 2 and 3) so that the cells could be pushed to higher cell densities. The reactor volume was held constant by using a weight control system to add the same amount of feed to the reactor that was being removed in the perfusate using the ATF4 system, by monitoring the weight of the system and using a computer feedback control system to maintain a weight within plus or minus 0.05 kg of a given target.

RAMAN control and automated bleed control based on the RAMAN feedback was used to control VCC in this run (FIG. 15). In a first experiment (Ex. 9), the RAMAN bleed strategy was set to maintain a VCC of 40×10⁶ cells/mL. The range of the VCC was 35-45×10⁶ cells/mL, which was slightly wider than the target that occurred with the manual bleed in the previous experiment (Example 3). However, the system was only sampled once a day and no adjustments were needed in this perfusion run (as compared to multiple times a day with multiple adjustments with the manual bleed described in Example 3).

In a second experiment (Ex. 10), the conditions were analogous to the first experiment except VCC was set at 10×10⁶ cells/mL with a perfusion rate of one reactor volume per day.

Example 6 (FIGS. 19 and 20)

In one experiment, three different bioreactors were cultured using cell lines and medium. The capacity of the bioreactors were: 3 L (Ex. 11), 15 L (Ex. 12), and 50 L (Ex. 13) (single-use bioreactor). The bioreactor set points included temperature (35.5 degrees Celsius), agitation (250 RPM), pH (controlled using CO2 and sodium bicarbonate) (from 6.85 to 7.15), and working volume (2 L, 10 L, 35 L, respectively). All of these parameters were held constant for the duration of the run. Each bioreactor was coupled with an ATF (ATF2, ATF4, ATF6, respectively) Cell Retention Device equipped with 0.2 micron filter. The hollow fiber filter retained cells but allowed protein to pass through after 24 hours.

A perfusion culture was performed in each system using RAMAN, bleed, and weight control at all three scales. As with Example 5, the medium in this experiment was supplemented with extra nutrients. The weight within each system was controlled to: +/−0.05 kg in the ATF4 and ATF6, and +/−1 kg (due to equipment limitations of the scale itself) of a given target.

RAMAN control and automated bleed control based on RAMAN feedback was used to set the VCC in this run (FIG. 19) to 40×10^6 cells/m L. RAMAN probe variability was observed in the 50 L ATF6 system, which is expected since the RAMAN control model had not yet been optimized for the large scale.

Within all three of these runs, the perfusion rate was set between 1.8 and 2 RV/day, and all scale-up parameters were set using traditional methods.

The results of this experiment were that a comparable protein productivity (FIG. 20) was achieved in all three systems for a duration of five days.

Example 7 (FIG. 21)

In one experiment, a single bioreactor was cultured using cell lines and medium. The capacity of the bioreactor was 15 L (Ex. 14). The bioreactor set points included temperature (35.5 degrees Celsius), agitation (250 RPM), pH (controlled using CO2 and sodium bicarbonate) (from 6.85 to 7.15). All of these parameters were held constant for the duration of the run. The bioreactor was coupled with an ATF4 Cell Retention Device equipped with 0.2 micron filter. The hollow fiber filter retained cells but allowed protein to pass through after 24 hours.

A perfusion culture was performed in the system using RAMAN, bleed, and weight control. As with Example 5, the medium in this experiment was supplemented with extra nutrients. The weight within each system was controlled to: +/−0.05 kg in the ATF4 of a given target.

RAMAN control and automated bleed control based on RAMAN feedback was used to set the VCC in this run (see FIG. 21) to 70×10^6 cells/m L.

The perfusion rate in this run was set at 2.5 RV/day to supplement the extra cells in culture, and ensure that medium depletion would not occur.

The reactor was able to maintain a VCC above 70×10^6 cells/mL for 7 days before an equipment failure lead to the end of the batch. During this time viabilities were maintained above 90% indicating a healthy culture. Before implementation of the control system of this disclosure, sustained production at such high densities would not have been possible.

Notably, reference herein to "one embodiment," or "an embodiment" means that a particular feature, structure, or characteristic described in connection with the embodiment may be included, employed and/or incorporated in one, some or all of the embodiments of the present disclosure. The usages or appearances of the phrase "in one embodiment" or "in another embodiment" in the specification are not referring to the same embodiment, nor are separate or alternative embodiments necessarily mutually exclusive of one or more other embodiments, nor limited to a single exclusive embodiment. The same applies to the terms "implementation," and "example." The present disclosure are neither limited to any single aspect nor embodiment thereof, nor to any combinations and/or permutations of such aspects and/or embodiments. Moreover, each of the aspects of the present disclosure, and/or embodiments thereof, may be employed alone or in combination with one or more of the other aspects of the present disclosure and/or embodiments thereof. For the sake of brevity, certain permutations and combinations are not discussed and/or illustrated separately herein.

Further, as indicated above, an embodiment or implementation described herein as "exemplary" is not to be construed as preferred or advantageous, for example, over other embodiments or implementations; rather, it is intended convey or indicate the embodiment or embodiments are example embodiment(s).

What is claimed is:

1. A method of controlling a bioreactor system, comprising:
   providing a cell culture in a perfusion bioreactor, wherein conditions in the perfusion bioreactor enable the cell culture to produce a protein of interest (POI);
   measuring one or more process parameters (PPs) of the culture within the perfusion bioreactor by a RAMAN probe, wherein the process parameters are selected from the group consisting of nutrient concentration, viable cell concentration, and protein attributes;
   measuring a weight of the perfusion bioreactor with cell culture contents;
   removing cell-free spent media from the cell culture using a first output conduit at a first specified rate;
   removing cells from the cell culture using a second output conduit at a second specified rate;
   introducing one or both of fresh media or nutrients into the cell culture using an input conduit at a third specified rate; and
   adjusting at least one of the specified rates in response to a corresponding change in another one of the specified rates to maintain a perfusion rate of the perfusion bioreactor at a constant perfusion rate setpoint, wherein the perfusion rate defines a rate of total flow through the perfusion bioreactor such that the rate of total flow remains constant when the at least one specified rate is adjusted;
   wherein the input and output conduits are adjusted based on the RAMAN probe measurements and weight measurement of the perfusion bioreactor to maintain (i) one or more of the process parameters within predetermined ranges, (ii) the weight of the perfusion bioreactor with the cell culture within a predetermined range, (iii) the third specified rate of the input conduit and the first and second specified rates of each of the output conduits within their respective predetermined ranges, and (iv) the perfusion rate of the perfusion bioreactor at the constant perfusion rate setpoint.

2. The method of claim 1, wherein prior to adjusting the at least one of the specified rates, the method comprises:
   determining a feedback loop, based on the one or more process parameters measured by the RAMAN probe, that increases or decreases the at least one specified rate in response to an opposing decrease or increase of the other specified rate, respectively;
   wherein measuring the one or more process parameters of the culture within the perfusion bioreactor by RAMAN occurs at least once per hour.

3. The method of claim 1, wherein the method is configured to maintain the cell culture at an average viable cell concentration of at least 30 million cells per mL for 30 days at steady state.

4. The method of claim 1, wherein the perfusion bioreactor has a volume of at least 10 L, and the method is configured to maintain the weight of the perfusion bioreactor and cell culture within a 20 g range.

5. The method of claim 1, wherein the perfusion bioreactor has a volume of at least 10 L, and the method is configured to maintain the weight of the perfusion bioreactor with the cell culture within 0.1 percent of an initial weight of the perfusion bioreactor with the cell culture.

6. The method of claim 1, wherein, when a process parameter deviates from a set point value within a respective desired range, one or more of removing cell-free media, removing cells, or introducing one or both of fresh media or nutrients, is adjusted to reduce the deviation.

7. The method of claim 1, wherein at least two bioreactor volumes of spent media are removed through the first output conduit per day, and the constant perfusion rate setpoint is selected from one to three bioreactor volumes per day.

8. The method of claim 1, wherein the process parameters include temperature of the cell culture and pH of the cell culture, and the temperature is maintained between 35 and 36 degrees C., and the pH is maintained between 6.85 and 7.15.

9. The method of claim 1, wherein the process parameters include cell specific productivity, and the method is configured to maintain cells within the cell culture at a cell specific productivity of at least 15 pg/cell/day for at least 25 days.

10. The method of claim 1, wherein the process parameters include glucose concentration, and the method is configured to maintain a glucose concentration between about 5 mM to about 85 mM, or about 1 g/L to about 15.5 g/L.

11. The method of claim 1, wherein the process parameters include lactate concentration, and the method is configured to maintain a lactate concentration less than about 60 mM, or less than about 6 g/L.

12. The method of claim 1, wherein the process parameters include ammonia concentration, and the method is configured to maintain an ammonia concentration less than about 15 mM.

13. The method of claim 1, wherein each of removing cell-free spent media, removing cells, and introducing one or both of fresh media or nutrients, is controlled by a respective pump.

14. The method of claim 1, wherein the perfusion bioreactor includes a filter configured to retain cells and allow fluid to pass through.

15. A method of controlling a bioreactor system, comprising:
providing a cell culture in a perfusion bioreactor;
measuring one or more process parameters of the cell culture within the perfusion bioreactor by a RAMAN probe;
removing cell-free spent media from the cell culture using a first output conduit at a first specified rate;
removing cells from the cell culture using a second output conduit at a second specified rate;
introducing one or both of fresh media or nutrients into the cell culture using an input conduit at a third specified rate; and
determining a first change to one or more of the first specified rate, the second specified rate, or the third specified rate based on the RAMAN probe measurements;
applying a second change to another one of the first specified rate, the second specified rate, or the third specified rate in response to the first change to maintain a perfusion rate through the perfusion bioreactor at a constant perfusion rate setpoint such that a total input and a total output of the perfusion bioreactor remains constant during the first change and the second change;
wherein the input and output conduits are automatically adjusted, by a controller receiving the RAMAN probe measurements of the perfusion bioreactor to maintain (i) one or more of the process parameters within predetermined ranges, (ii) the first specified rate and the second specified rate of each of the output conduits within respective predetermined ranges, (iii) the third specified rate of the input conduit within a predetermined range; and (iv) the perfusion rate of the perfusion bioreactor based on the constant perfusion rate setpoint.

16. The method of claim 1, wherein:
the perfusion bioreactor has a volume of at least 10 L and includes a filter configured to retain cells and allow fluid to pass through;
each of removing cell-free spent media, removing cells, and introducing one or both of fresh media or nutrients, is controlled by a respective pump; and
the method is configured to maintain the weight of the perfusion bioreactor with the cell culture within 0.1 percent of an initial weight of the perfusion bioreactor with the cell culture, and the constant perfusion rate setpoint is selected from one to three bioreactor volumes per day.

17. The method of claim 16, wherein:
the method is configured to maintain the cell culture at an average viable cell concentration of at least 30 million cells per mL for 30 days at steady state; and
when a process parameter deviates from a set point value within a respective desired range, one or more of removing cell-free media, removing cells, or introducing one or both of fresh media or nutrients, is adjusted to reduce the deviation and maintain the constant perfusion rate constant at two times the bioreactor volume per day.

18. The method of claim 17, wherein:
at least two bioreactor volumes of spent media are removed through the first output conduit per day;
the process parameters include temperature of the cell culture and pH of the cell culture, the temperature is maintained between 35 and 36 degrees C., and the pH is maintained between 6.85 and 7.15; and
the process parameters include cell specific productivity, and the method is configured to maintain cells within the cell culture at a cell specific productivity of at least 15 pg/cell/day for at least 25 days.

19. The method of claim 18, wherein:
the process parameters include glucose concentration, and the method is configured to maintain a glucose concentration between about 5 mM to about 85 mM, or about 1 g/L to about 15.5 g/L;
the process parameters include lactate concentration, and the method is configured to maintain a lactate concentration less than about 60 mM, or less than about 6 g/L;
the process parameters include ammonia concentration, and the method is configured to maintain an ammonia concentration less than about 15 mM.

20. The method of claim 1, further comprising: wherein the input and output conduits are automatically adjusted, by one or more controllers, to maintain (i) one or more of the process parameters within predetermined ranges, (ii) the weight of the perfusion bioreactor with the cell culture within a predetermined range, and (iii) the third specified rate of the input conduit and the first and second specified rates of each of the output conduits within their respective predetermined ranges.

* * * * *

UNITED STATES PATENT AND TRADEMARK OFFICE
CERTIFICATE OF CORRECTION

PATENT NO. : 11,193,103 B2
APPLICATION NO. : 16/160465
DATED : December 7, 2021
INVENTOR(S) : Matthew Angelini et al.

It is certified that error appears in the above-identified patent and that said Letters Patent is hereby corrected as shown below:

On the Title Page

Item (73), in the first column under Assignee, delete "Regeneran" and insert --Regeneron--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*